(12) United States Patent
Sun et al.

(10) Patent No.: US 11,819,210 B2
(45) Date of Patent: Nov. 21, 2023

(54) DRIVING DEVICE, SURGICAL INSTRUMENT, AND OPERATION METHOD THEREOF

(71) Applicant: FULBRIGHT MEDICAL INC., Jiangsu (CN)

(72) Inventors: Baofeng Sun, Jiangsu (CN); Zhixing Zhang, Jiangsu (CN)

(73) Assignee: FULBRIGHT MEDICAL INC., Jiangsu (CN)

( * ) Notice: Subject to any disclaimer, the term of this patent is extended or adjusted under 35 U.S.C. 154(b) by 73 days.

(21) Appl. No.: 17/607,905

(22) PCT Filed: Apr. 30, 2020

(86) PCT No.: PCT/CN2020/088444
§ 371 (c)(1),
(2) Date: Nov. 1, 2021

(87) PCT Pub. No.: WO2020/221355
PCT Pub. Date: Nov. 5, 2020

(65) Prior Publication Data
US 2022/0265271 A1    Aug. 25, 2022

(30) Foreign Application Priority Data

May 1, 2019 (CN) .......................... 201910367362.7
May 1, 2019 (CN) .......................... 201910367363.1

(51) Int. Cl.
*A61B 17/072*  (2006.01)
*A61B 17/3209* (2006.01)
(Continued)

(52) U.S. Cl.
CPC .... *A61B 17/07207* (2013.01); *A61B 17/3209* (2013.01); *A61B 2017/00017* (2013.01);
(Continued)

(58) Field of Classification Search
CPC .................... A61B 17/072; A61B 2017/00367
See application file for complete search history.

(56) References Cited

U.S. PATENT DOCUMENTS 7,364,061 B2 *  4/2008  Swayze ............ A61B 17/07207
                                                                 227/176.1
2005/0125009 A1 *  6/2005  Perry ................. A61B 17/2909
                                                                    606/139
(Continued)

FOREIGN PATENT DOCUMENTS

CN         1868411 A    11/2006
CN      101475066 A     7/2009
(Continued)

*Primary Examiner* — Gloria R Weeks
(74) *Attorney, Agent, or Firm* — Gang Yu

(57) ABSTRACT

A driving device, a surgical instrument, and an operation method of the surgical instrument. The driving device is driven by a power assembly. The driving device comprises a first driving assembly and a first motion conversion assembly. The first driving assembly comprises a first effective stroke structure and a first idle stroke structure. The driving device has a first state and a second state. In the first state, the power assembly is engaged with the first effective stroke structure, and the first effective stroke structure drives the first motion conversion assembly; in the second state, the power assembly is coupled with the first idle stroke structure, and the first motion conversion assembly is disengaged from the driving of the power assembly.

19 Claims, 24 Drawing Sheets

First direction

(51) Int. Cl.
 *A61B 90/00* (2016.01)
 *A61B 17/00* (2006.01)
 *A61B 17/29* (2006.01)
(52) U.S. Cl.
 CPC ............... *A61B 2017/00398* (2013.01); *A61B 2017/07271* (2013.01); *A61B 2017/07285* (2013.01); *A61B 2017/2923* (2013.01); *A61B 2090/0811* (2016.02)

(56) References Cited

U.S. PATENT DOCUMENTS

| | | | |
|---|---|---|---|
| 2008/0314954 | A1 | 12/2008 | Boudreaux |
| 2011/0290851 | A1* | 12/2011 | Shelton, IV ..... A61B 17/07207 227/176.1 |
| 2011/0290854 | A1* | 12/2011 | Timm .................. A61B 17/068 227/178.1 |
| 2012/0074201 | A1* | 3/2012 | Baxter, III ....... A61B 17/07207 606/1 |
| 2014/0014704 | A1* | 1/2014 | Onukuri ............... C10M 169/00 227/175.1 |
| 2014/0014707 | A1 | 1/2014 | Onukuri et al. |
| 2014/0263539 | A1* | 9/2014 | Leimbach ............. G16H 20/40 227/175.1 |
| 2014/0305989 | A1* | 10/2014 | Parihar ................ A61B 17/068 227/176.1 |
| 2015/0209035 | A1* | 7/2015 | Zemlok ........... A61B 17/07207 73/1.01 |
| 2016/0100838 | A1* | 4/2016 | Beaupré ........... A61B 17/07207 227/175.1 |
| 2016/0287253 | A1* | 10/2016 | Shelton, IV ..... A61B 17/07292 |
| 2016/0317215 | A1 | 11/2016 | Worrell et al. |
| 2016/0374666 | A1 | 12/2016 | Dinardo et al. |
| 2016/0374681 | A1* | 12/2016 | Miller .................. A61B 17/105 227/176.1 |
| 2021/0353290 | A1* | 11/2021 | Fernandes ........ A61B 17/07207 |

FOREIGN PATENT DOCUMENTS

| | | |
|---|---|---|
| CN | 201879763 U | 6/2011 |
| CN | 103702623 A | 4/2014 |
| CN | 105307577 A | 2/2016 |
| CN | 105943104 A | 9/2016 |
| CN | 105997171 A | 10/2016 |
| CN | 106108964 A | 11/2016 |
| CN | 106580378 A | 4/2017 |
| CN | 106659499 A | 5/2017 |
| CN | 107530082 A | 1/2018 |
| CN | 109248436 A | 1/2019 |
| EP | 2944276 A1 | 11/2015 |
| WO | 2018106406 A1 | 6/2018 |

* cited by examiner

First direction

DRIVING DEVICE, SURGICAL INSTRUMENT, AND OPERATION METHOD THEREOF

CROSS-REFERENCE TO RELATED APPLICATION(S)

The present disclosure is a national stage application of International Patent Application No. PCT/CN2020/088444, which is filed on Apr. 30, 2020, and claims priority to Chinese Patent Application No. 201910367363.1, filed on May 1, 2019, and claims priority to Chinese Patent Application No. 201910367362.7, filed on May 1, 2019.

TECHNICAL FIELD

The disclosure relates to a driving device, an end actuator driving device, a surgical instrument driving device, a surgical instrument and an operation method of the surgical instrument.

BACKGROUND

As is well known, an intracavitary cutting stapler has been commonly used in the abdominal cavity and other intracavitary operations.

An intracavitary cutting stapler known to inventors generally includes an operation assembly, a rod assembly extending longitudinally from the operation assembly, and an end effector disposed at a distal end of the rod assembly. The stapler further includes a trigger and a motor assembly. The trigger is manipulated to open and close the end effector. The stapler also includes a cutting knife assembly, and the trigger may also be manipulated to drive the cutting knife assembly to move forwards and backwards. The end effector includes a staple cartridge seat for operably supporting a staple cartridge therein and a staple abutting seat pivotally connected to the staple cartridge seat, the staple abutting seat is selectively movable between an open position and a closed position.

The operation assembly includes a body and a driving device mounted to the body for driving the end effector to be opened or closed. When the surgical instrument is used, the end effector is required to clamp tissue, in the process of clamping the tissue by the end effector, reverse force of the tissue to the end effector is transmitted to the driving device, and the reverse force may reduce the driving efficiency of the driving device.

SUMMARY

Some embodiments provide a driving device with higher driving efficiency.

In order to achieve the purpose, some embodiments of the disclosure are realized by the following technical solution.

A driving device is driven by a power assembly. The driving device includes a first driving assembly and a first motion conversion assembly. The first driving assembly includes a first effective stroke structure and a first idle stroke structure. The driving device has a first state and a second state. In the first state, the power assembly is engaged with the first effective stroke structure, and the first effective stroke structure drives the first motion conversion assembly; and in the second state, the power assembly is coupled with the first idle stroke structure, and the first motion conversion assembly is disengaged from the driving of the power assembly.

In some embodiments, the first motion conversion assembly includes a first transmission member and a first output member, and in the first state, the first transmission member drives the first output member to move; and in the second state, the first output member is not driven.

In some embodiments, the first driving assembly includes a first driving member and a rotating member, and in the first state, the first driving member and the rotating member are engaged with the power assembly; and in the second state, only the first driving member in the first driving member and the rotating member is engaged with the power assembly.

In some embodiments, the first motion conversion assembly includes a first transmission member and a first output member engaged with the first transmission member, and the first transmission member is disposed on the rotating member.

In some embodiments, the first effective stroke structure and the first idle stroke structure are both disposed on the rotating member, and in the first state, the first effective stroke structure and the first driving member both are engaged with the power assembly; and in the second state, the first idle stroke structure is coupled with the power assembly, and the first driving member is engaged with the power assembly.

In some embodiments, the first effective stroke structure is a toothed portion, the first idle stroke structure is a non-toothed portion, and the toothed portion and the non-toothed portion are disposed adjacently; and the first driving member is a first driving gear.

In some embodiments, the power assembly includes a motor and a front driving gear driven by the motor, and in the first state, the front driving gear is meshed with the toothed portion and the first driving gear simultaneously; and in the second state, the front driving gear is coupled with the non-toothed portion, and is meshed with the first driving gear.

In some embodiments, the first driving member and the rotating member are overlapped, one of the first driving member and the rotating member is provided with an arc groove, the other is provided with a protrusion extending into the arc groove, and the circle center of the arc groove is located on the rotation axis of the first driving member.

In some embodiments, the width of the protrusion is smaller than that of the arc groove.

In some embodiments, the protrusion abuts against the end portion of the arc groove so that the rotating member and the first driving member are switched from the second state to a ready position of the first state.

In some embodiments, the first motion conversion assembly includes a first groove and a protruding column, a radial distance between the first groove and the rotation center of the rotating member increases or decreases along the first groove, and the protruding column slides in the first groove to convert rotation of the rotating member into linear motion of the protruding column.

In some embodiments, the first groove is disposed on the rotating member.

An end effector driving device, including the driving device of any of the above, and the driving device is configured to drive an end effector to be opened or closed.

In some embodiments, the first effective stroke structure includes a first portion and a second portion which are disposed adjacently, the first portion drives the end effector to execute a first stage of closing to clamp tissue, and the second portion drives the end effector to execute a second stage of closing to press the tissue.

In some embodiments, the first motion conversion assembly includes a first transmission member and a first output member engaged with the first transmission member, and the first transmission member includes a first section and a second section which are disposed adjacently; the first portion is engaged with the power assembly, so that the first output member is engaged with the first section; and the second portion is engaged with the power assembly, so that the first output member is engaged with the second section.

In some embodiments, the first transmission member also includes a third section adjacent to the second section, and the second section is located between the first section and the third section.

A surgical instrument driving device, including the end effector driving device of any of the above.

In some embodiments, the surgical instrument driving device also includes a cutting knife assembly driving device, which drives a cutting knife assembly to move forwards or backwards.

In some embodiments, the cutting knife assembly driving device is driven by the power assembly.

In some embodiments, the cutting knife assembly driving device includes a second effective stroke structure and a second idle stroke structure, and the power assembly drives one of the first effective stroke structure and the second effective stroke structure.

In some embodiments, the cutting knife assembly driving device includes a second driving assembly and a second motion conversion assembly engaged with the second driving assembly. The second motion conversion assembly includes a second transmission member and a second output member. The second transmission member includes a second effective stroke structure and a second idle stroke structure. The cutting knife assembly driving device has a third state and a fourth state. In the third state, the second effective stroke structure is engaged with the second output member, and in the fourth state, the second idle stroke structure is coupled with the second output member.

In some embodiments, the second driving assembly includes a second driving member, the second driving member and the second transmission member move synchronously, and in the third state and the fourth state, the second transmission member is always engaged with the power assembly through the second driving member.

In some embodiments, the second effective stroke structure is a toothed portion disposed on the second transmission member, the second idle stroke structure is a non-toothed portion disposed on the second transmission member, and the second output member is a rack.

In some embodiments, the surgical instrument driving device has a first work state and a second work state, and in the first work state, the first state and the fourth state operate simultaneously; and in the second work state, the second state and the third state operate simultaneously.

A surgical instrument, including a transmission mechanism, an end effector driven by the transmission mechanism, and a cutting knife assembly, and the transmission mechanism includes the surgical instrument driving device of any of the above.

An operation method of a surgical instrument, the surgical instrument is the abovementioned surgical instrument, the surgical instrument includes a power assembly, the power assembly includes a motor, and the operation method includes the following steps.

In S1, an output shaft of the motor rotates in a first direction, and the motor drives the first effective stroke structure and is coupled with the second idle stroke structure.

In S2, the output shaft of the motor continues to rotate in the first direction, and the motor drives the second effective stroke structure and is coupled with the first idle stroke structure.

In S3, the output shaft of the motor rotates in a second direction, the second direction is opposite to the first direction, and the motor drives the second effective stroke structure and is coupled with the first idle stroke structure.

In S4, the output shaft of the motor continues to rotate in the second direction, and the motor drives the first effective stroke structure and is coupled with the second idle stroke structure.

In some embodiments, S1 is executed so that the end effector is closed; S2 is executed to enable the cutting knife assembly to advance; S3 is executed to enable the cutting knife assembly to retract; and S4 is executed to enable the end effector to be opened.

Some embodiments of the disclosure have the beneficial effects that in the second state, the first motion conversion assembly is disengaged from the driving of the power assembly, such that a reverse force received by the motion conversion assembly is not transmitted to the power assembly by the first driving assembly, thereby avoiding the impact thereof on the driving efficiency of the driving device.

DETAILED DESCRIPTION OF THE EMBODIMENTS

In order to make the purpose, technical solutions and advantages of the disclosure clearer, the disclosure will be further described below in combination with the drawings and embodiments. It is to be understood that the specific embodiments described herein are for the purpose of explaining the disclosure only and are not intended to limit the disclosure. All other embodiments obtained by those of ordinary skill in the art based on the embodiments of the disclosure without creative efforts shall fall within the protection scope of the disclosure.

Figure 1:
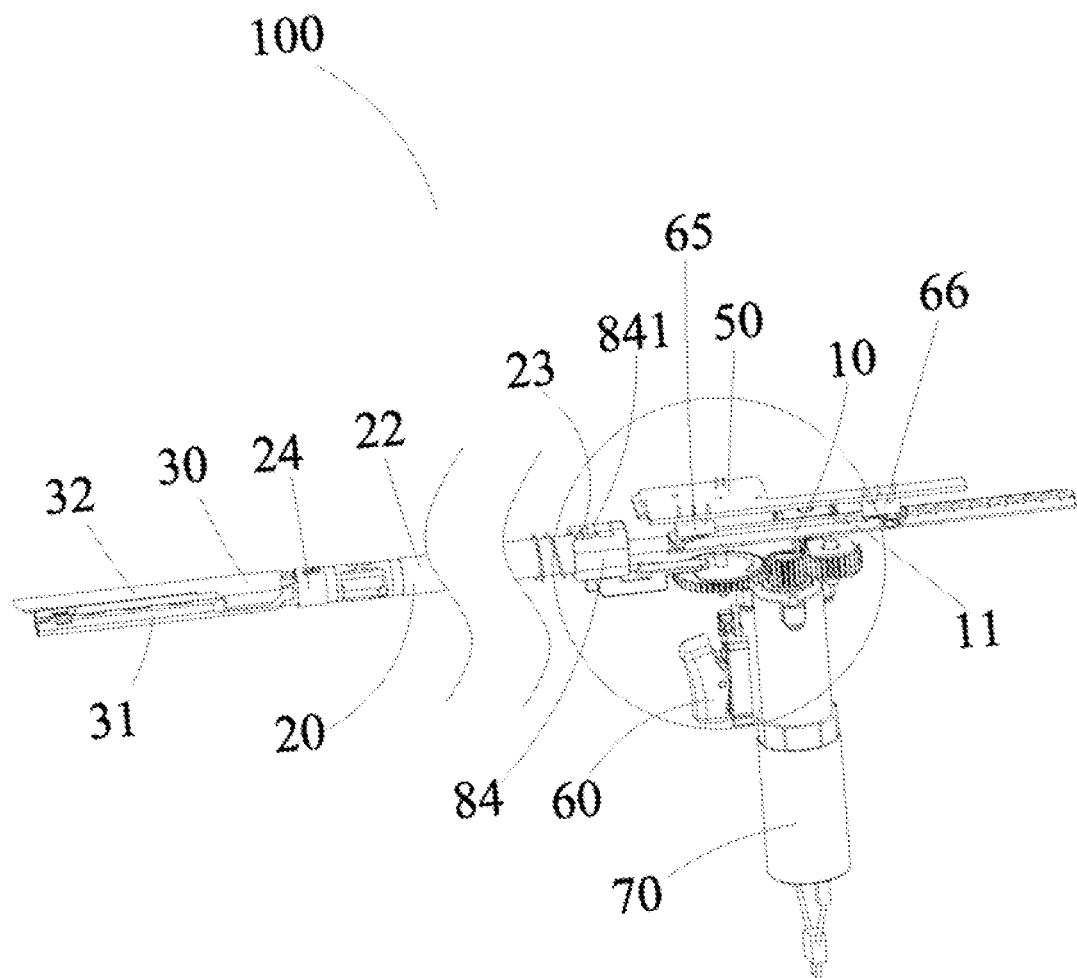
FIG. 1 illustrates a structural schematic diagram of a stapler according to a first embodiment of the disclosure.
Figure 1:
Figure 2:
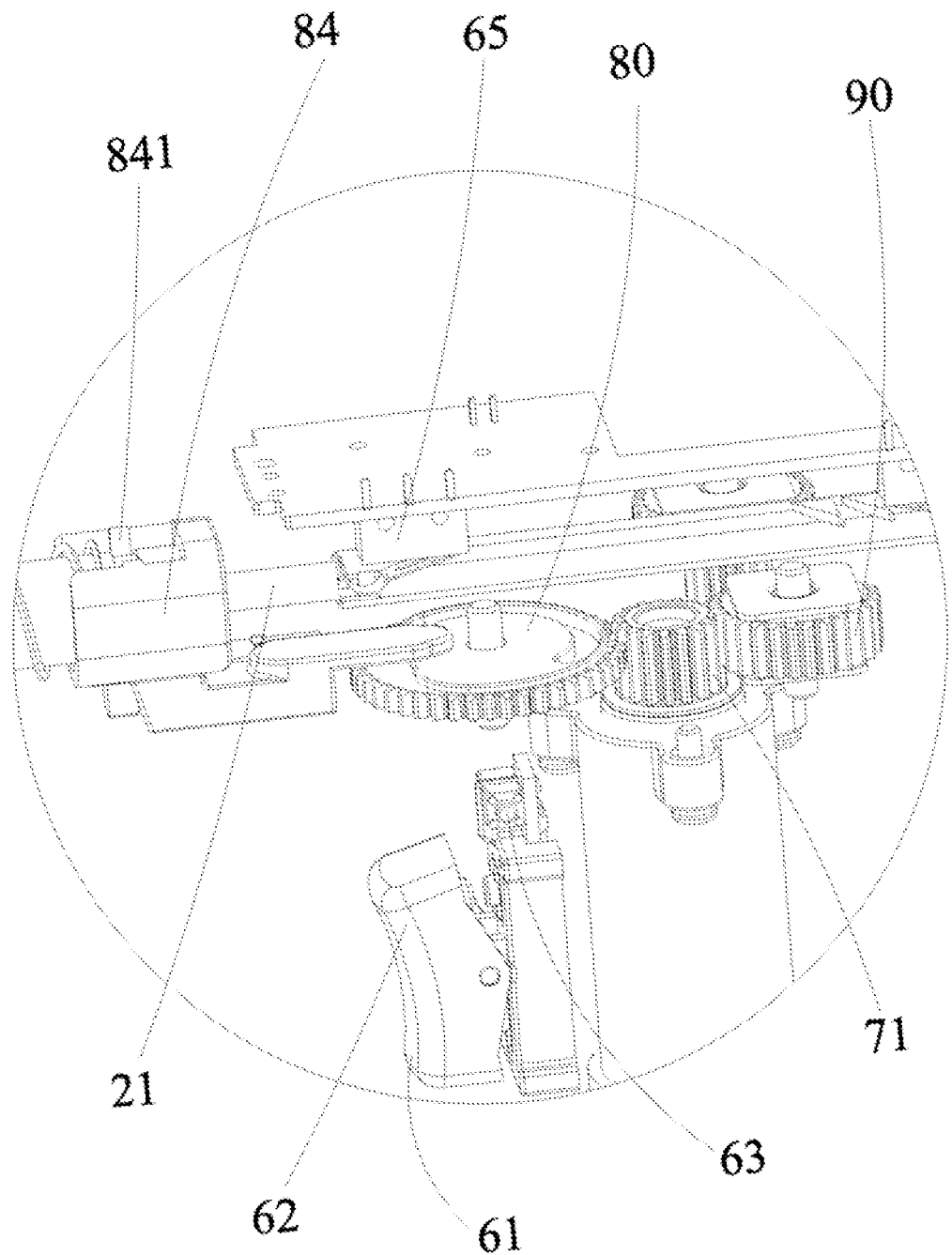
FIG. 2 illustrates an enlarged view of a circled portion as shown in FIG. 1.

The terms "proximal," "posterior," and "distal," "anterior" are used herein with reference to a clinician manipulating a surgical instrument. The terms "proximal" and "posterior" refer to portions relatively close to the clinician, and the terms "distal" and "anterior" refer to portions relatively far from the clinician. "Left" and "right" are referenced to the position of the surgical instrument as shown in FIG. 1, e.g., an end effector is on the "left" and a sleeve is on the "right". The terms "upper" and "lower" are referenced to the relative positions of a staple abutting seat and a staple cartridge seat of the end effector, specifically, the staple abutting seat is "upper", and the staple cartridge seat is "lower". It is to be understood that the orientation terms "proximal," "posterior," "distal," "anterior," "left," "right," "upper" and "lower" are defined for convenience of description, however, the surgical instrument may be used in many orientations and positions, and thus these terms expressing relative positional relationships are not intended to be limiting and absolute.

Figure 10:
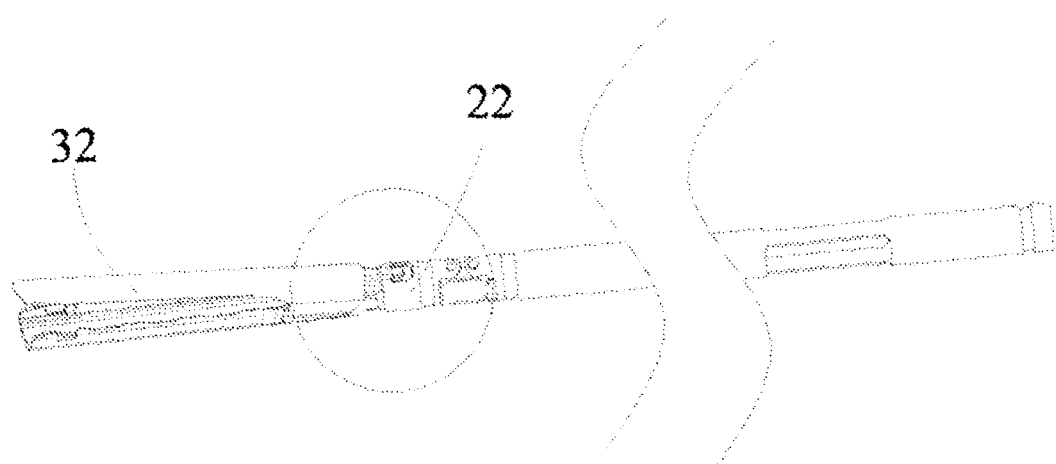
FIG. 10 illustrates an assembled diagram of an end effector and a sleeve as shown in FIG. 1.
Figure 11:
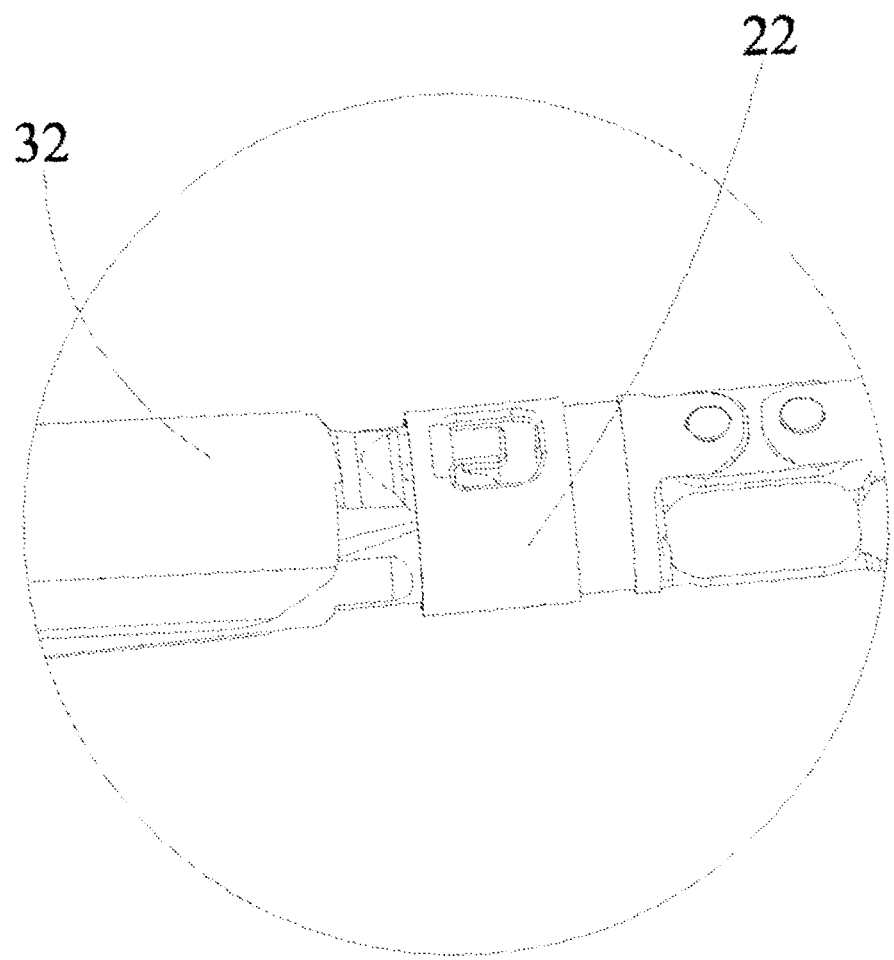
FIG. 11 illustrates an enlarged view of a circled portion as shown in FIG. 10.

As shown in FIGS. 1-14, a stapler 100 according to a first embodiment of the disclosure includes an operation assembly 10, a rod assembly 20 extending longitudinally from the operation assembly and an end effector 30 disposed at one end of the rod assembly 20. The end effector 30 includes a staple cartridge seat 31 and a staple abutting seat 32 pivotally connected to the staple cartridge seat 31, the staple cartridge seat 31 is used for operably supporting the staple cartridge (not shown in the figure), the staple abutting seat 32 is selectively movable between an open position and a closed position. The operation assembly 10 includes a body (not shown in the figure) and a transmission mechanism 11 mounted on the body. The rod assembly 20 includes a mandrel 21 and a sleeve 22 sleeving the mandrel 21, one end of the mandrel 21 is connected with a rack of a second driving device, and the other end of the mandrel 21 is located in the sleeve 22; the sleeve 22 includes a first end portion 23 connected to a first driving device and a second end portion 24 connected to the staple abutting seat 32 of the end effector 30, backward movement of the sleeve 22 enables the staple abutting seat 32 to pivot upwards so as to open the end effector 30, and forward movement of the sleeve 22 enables the staple abutting seat 32 to pivot downwards to close the end effector 30. Referring to FIGS. 10 and 11, the staple abutting seat 32 is rotatably connected to the second end portion 24 of the sleeve 22, i.e., the staple abutting seat 32 is connected to the second end portion 24 of the sleeve 22 and the staple abutting seat 32 is rotatable relative to the second end portion 24 of the sleeve 22. It is to be noted that the staple abutting seat 32 is rotatably connected to the second end portion 24 of the sleeve 22, so that forward and backward movement of the sleeve 22 drives the staple abutting seat 32 to pivot belongs to a relevant art.

Referring to FIGS. 10-11 and 15-20, the second end portion 24 of the sleeve 22 is movably connected to the staple abutting seat 32, and the staple abutting seat 32 is driven to pivot upwards to open the end effector 30 when the sleeve 22 moves towards a proximal end; and the staple abutting seat 32 is driven to pivot downwards to close the end effector 30 when the sleeve 22 moves towards a distal end.

Figure 15:
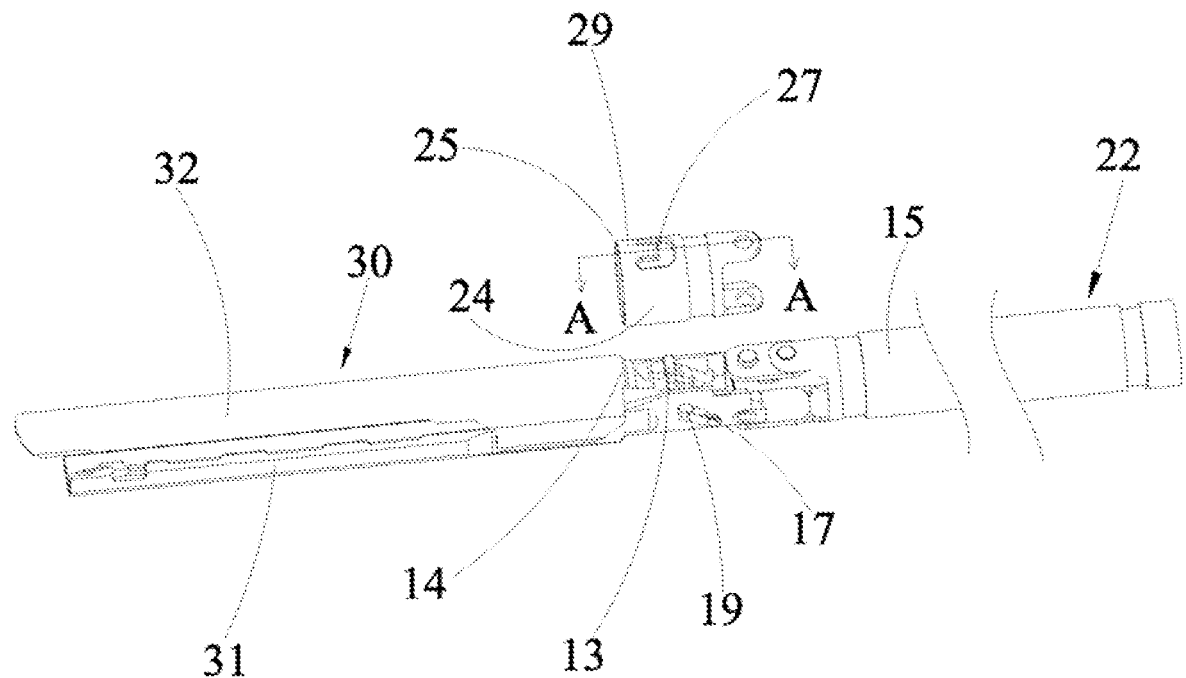
FIG. 15 illustrates a perspective view of the sleeve and the end effector of the stapler as shown in FIG. 1.
Figure 16:
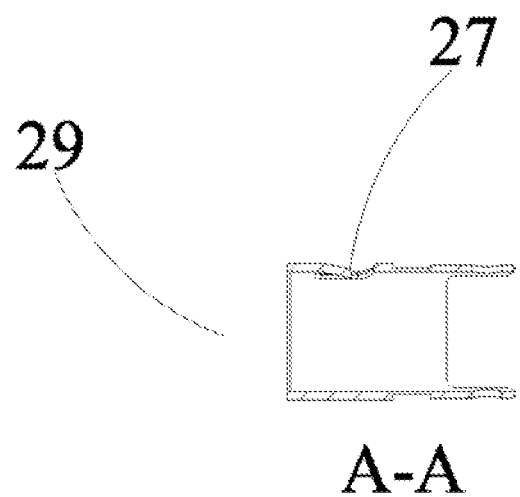
FIG. 16 illustrates a cross-sectional view of a driving tube of the sleeve as shown in FIG. 15 in a A-A direction.

In some embodiments, referring to FIGS. 15 and 16, the sleeve 22 includes a body 15 and a driving tube 29 which are connected, and the driving tube 29 drives the staple abutting seat 32 to pivot upwards or downwards to open or close the end effector 30. The body 15 and the driving tube 29 are connected by a hinge or may be integrally formed.

The driving tube 29 includes a first driving portion 27 for driving the staple abutting seat 32 to be opened and a second driving portion 25 for driving the staple abutting seat 32 to be closed. The first driving portion 27 is a protruding portion disposed on the driving tube 29, and the protruding portion obliquely extends along a lower right part; and the second driving portion 25 is a driving face at a distal end of the driving tube 29.

Correspondingly, the staple abutting seat 32 is provided with a first driven portion 13 capable of being cooperated with the first driving portion 27 and a second driven portion 14 capable of being cooperated with the second driving portion 25. The first driven portion 13 is a protruding portion disposed on the staple abutting seat 32, and the protruding portion extends upwards; and the second driven portion 14 is an abutting face at a proximal end of the staple abutting seat 32.

Figure 17:
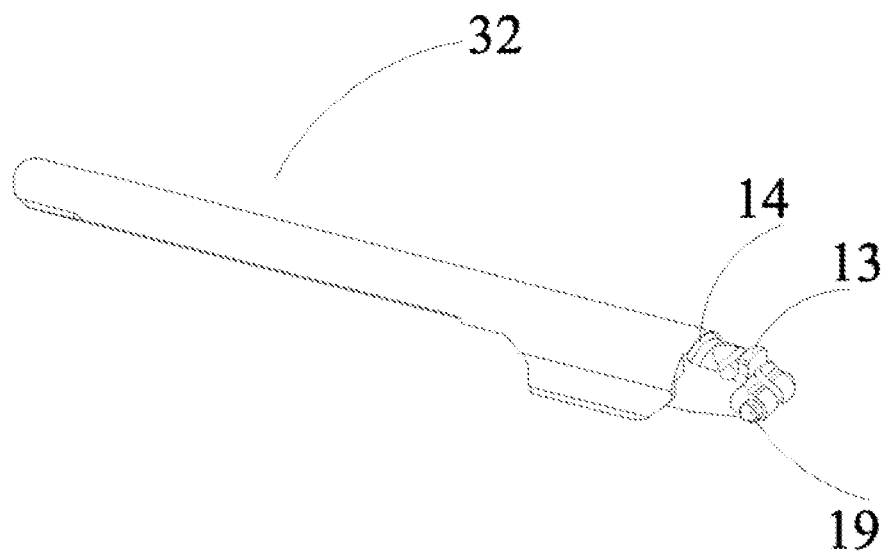
FIG. 17 illustrates a perspective view of a staple abutting seat of the surgical instrument as shown in FIG. 15.
Figure 18:
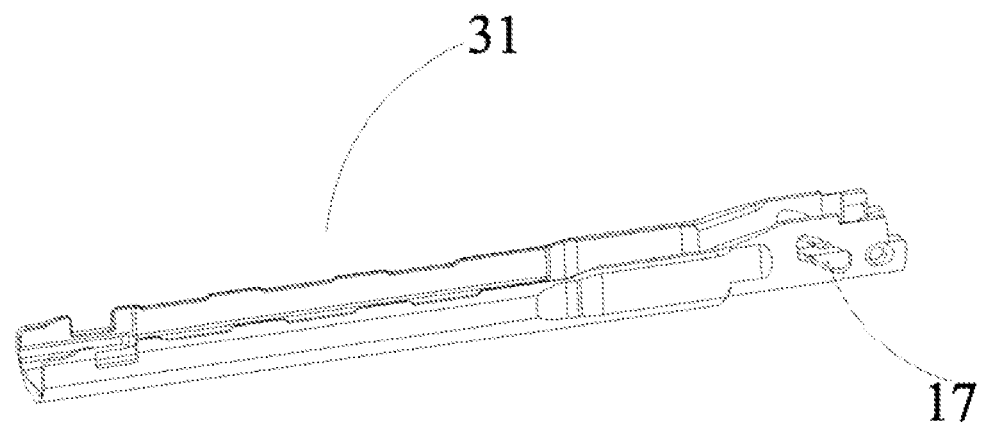
FIG. 18 illustrates a perspective view of a staple cartridge seat of the surgical instrument as shown in FIG. 15.

Referring to FIGS. 17 and 18, in some embodiments, a guide mechanism is further disposed between the staple abutting seat 32 and the staple cartridge seat 31, the guide mechanism includes a pin 19 disposed on the staple abutting seat 32 and a kidney-shaped groove 17 formed in the staple cartridge seat 31, and the kidney-shaped groove 17 obliquely extends upwards in a direction from the proximal end to the distal end.

Figure 19:
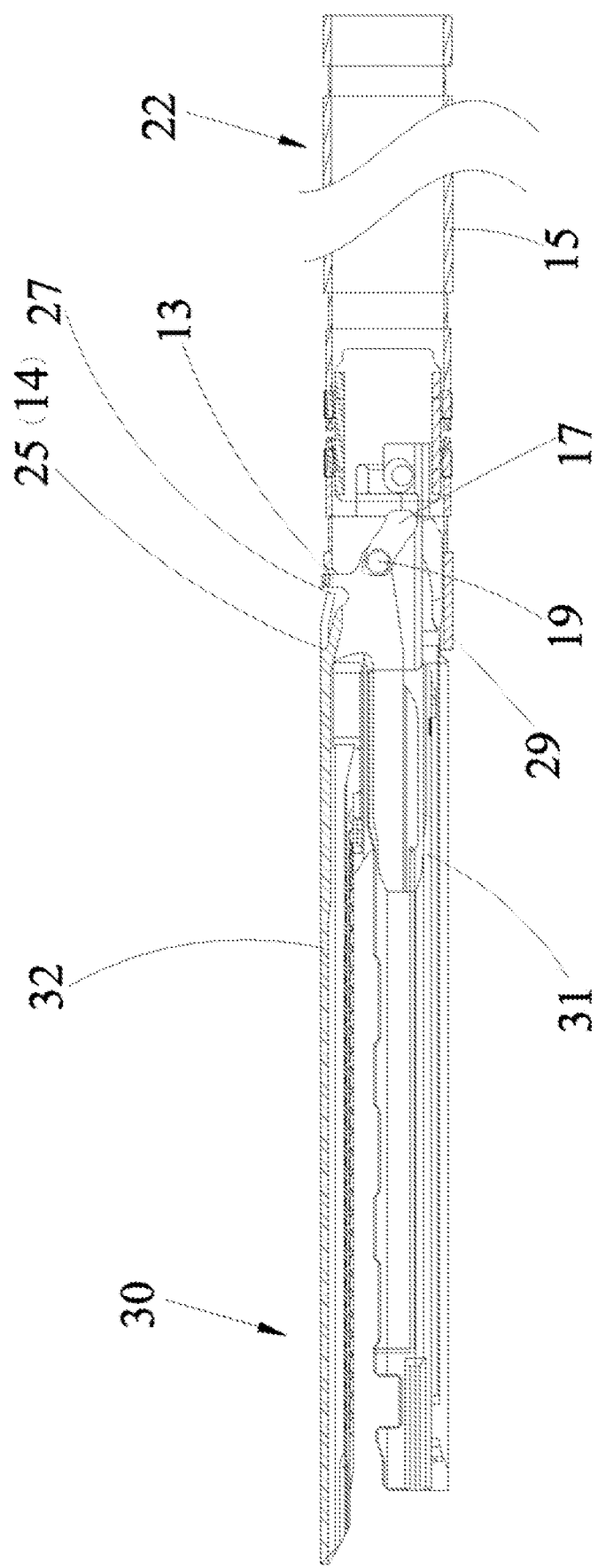
FIG. 19 illustrates a structural schematic diagram of the end effector of the surgical instrument as shown in FIG. 15 in a closed state.
Figure 20:
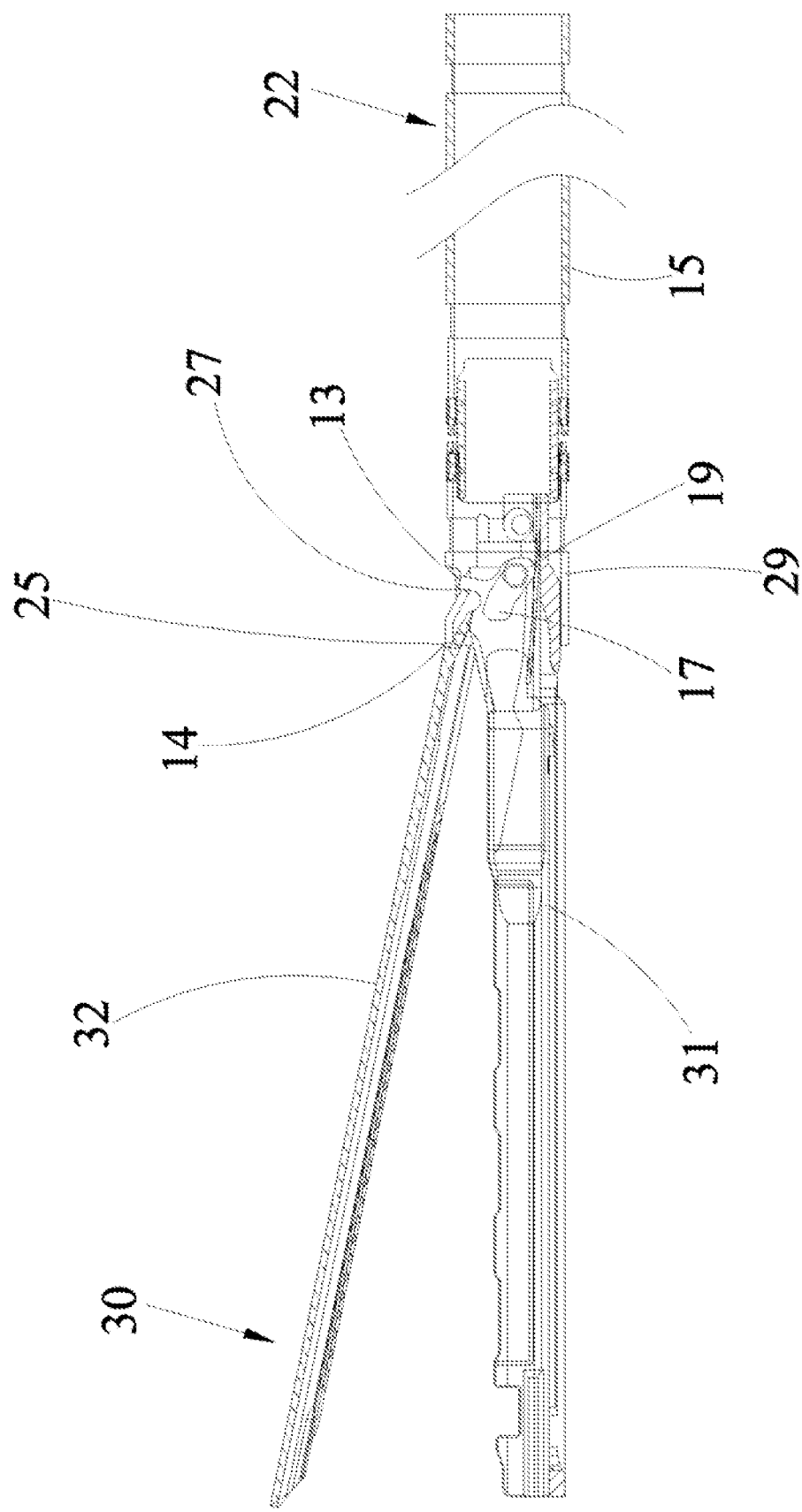
FIG. 20 illustrates a structural schematic diagram of the end effector of the surgical instrument as shown in FIG. 15 in an open state.

Referring to state changes of FIGS. 19-20, when the end effector 30 needs to be opened, the body 15 of the sleeve 22 pulls the driving tube 29 to move towards the proximal end, the first driving portion 27 on the driving tube 29 abuts against the first driven portion 13 on the staple abutting seat 32, the pin 19 moves from a distal upper end of the kidney-shaped groove 17 to a proximal lower end, the staple abutting seat 32 pivots upwards, and the end effector 30 is opened.

Referring to state changes of FIGS. 20-19, when the end effector needs to be closed, the body 15 of the sleeve 22 pushes the driving tube 29 to move towards the distal end, the second driving portion 25 on the driving tube 29 abuts against the second driven portion 14 on the staple abutting seat 32, the pin 19 moves from the proximal lower end of the kidney-shaped groove 17 to the distal upper end, the staple abutting seat 32 pivots downwards, and the end effector 30 is closed.

Figure 3:
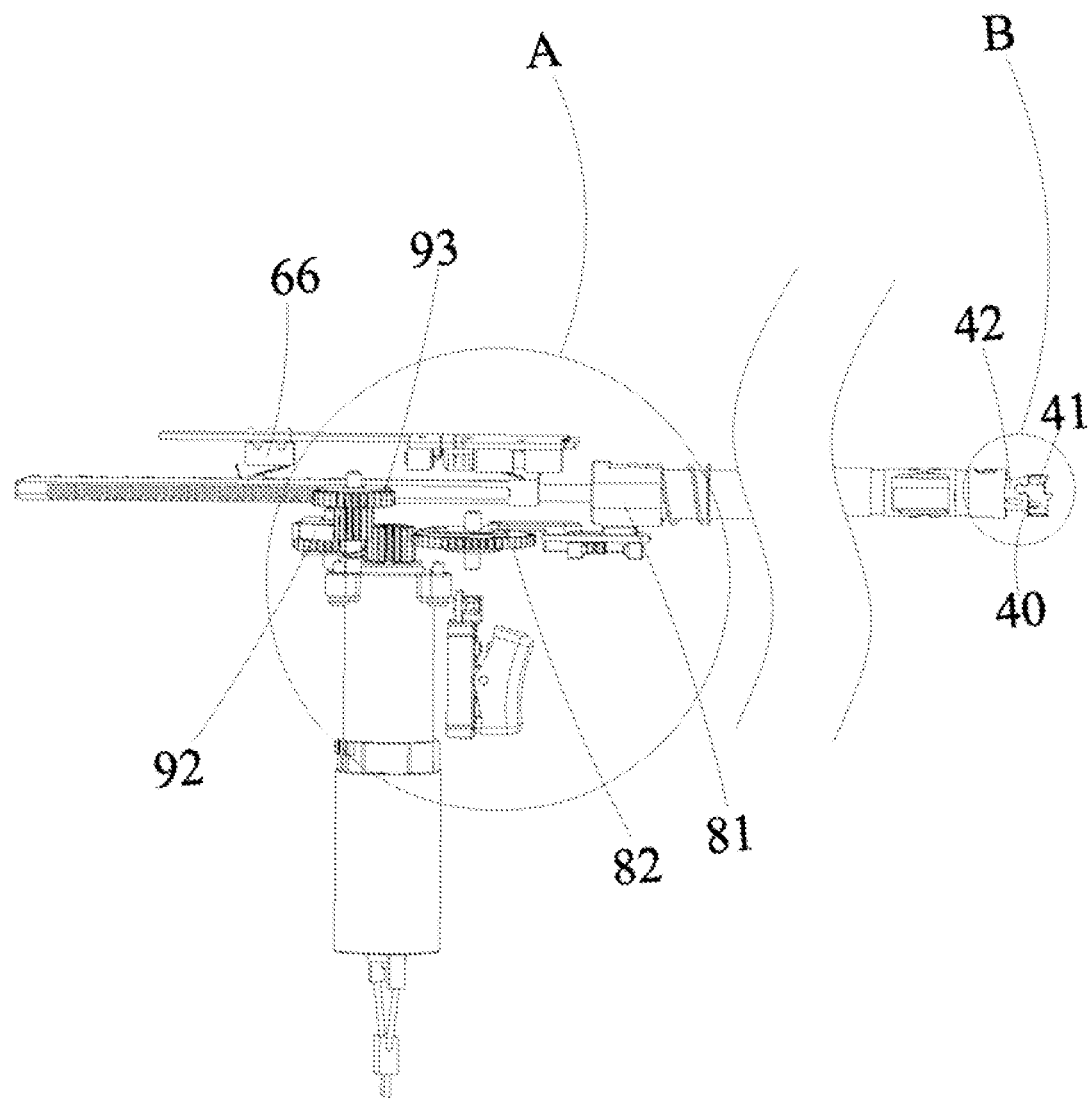
FIG. 3 illustrates a partial schematic diagram of the stapler as shown in FIG. 1 from another perspective.
Figure 4:
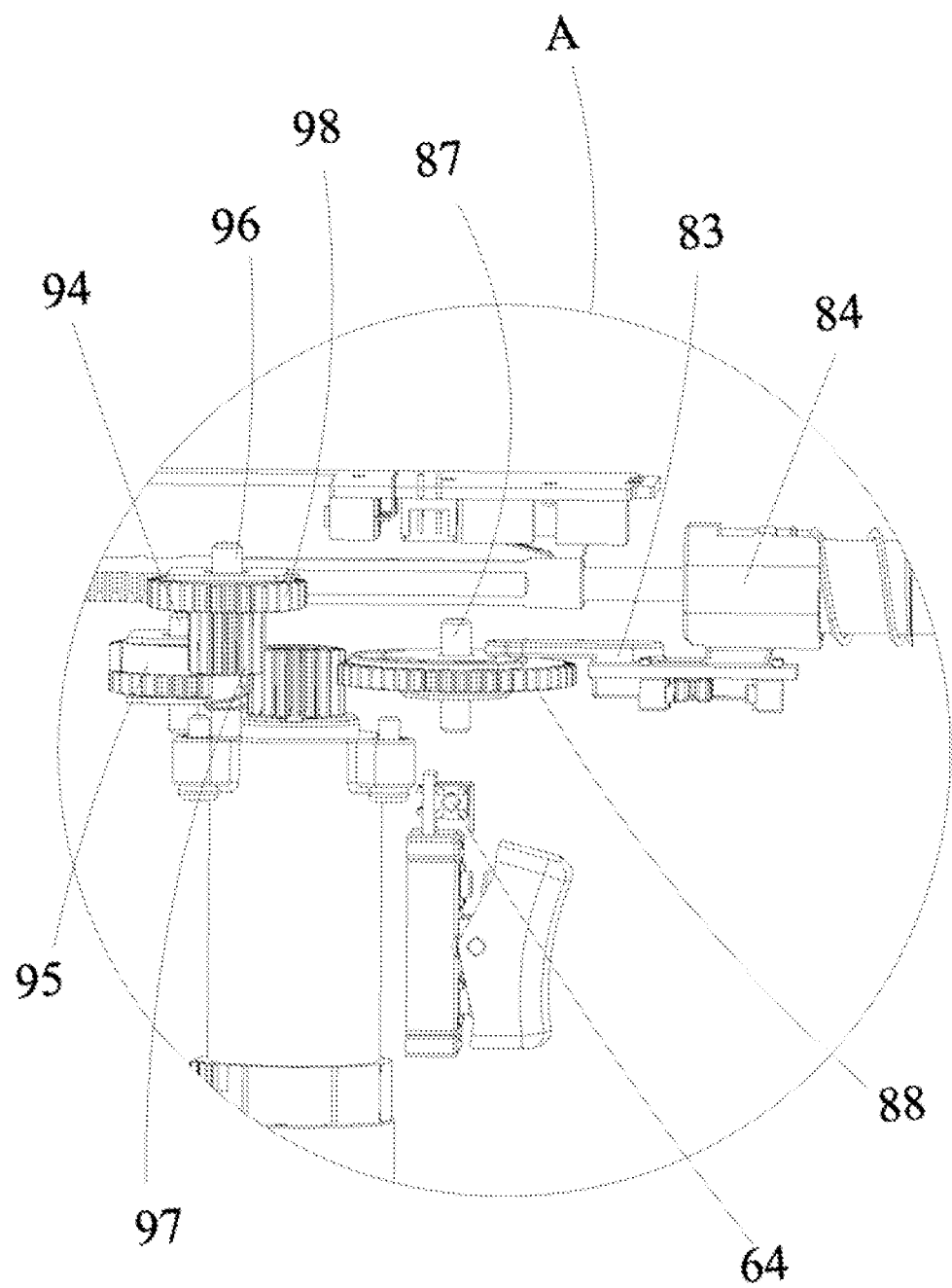
FIG. 4 illustrates an enlarged view of a circled portion A as shown in FIG. 3.
Figure 5:
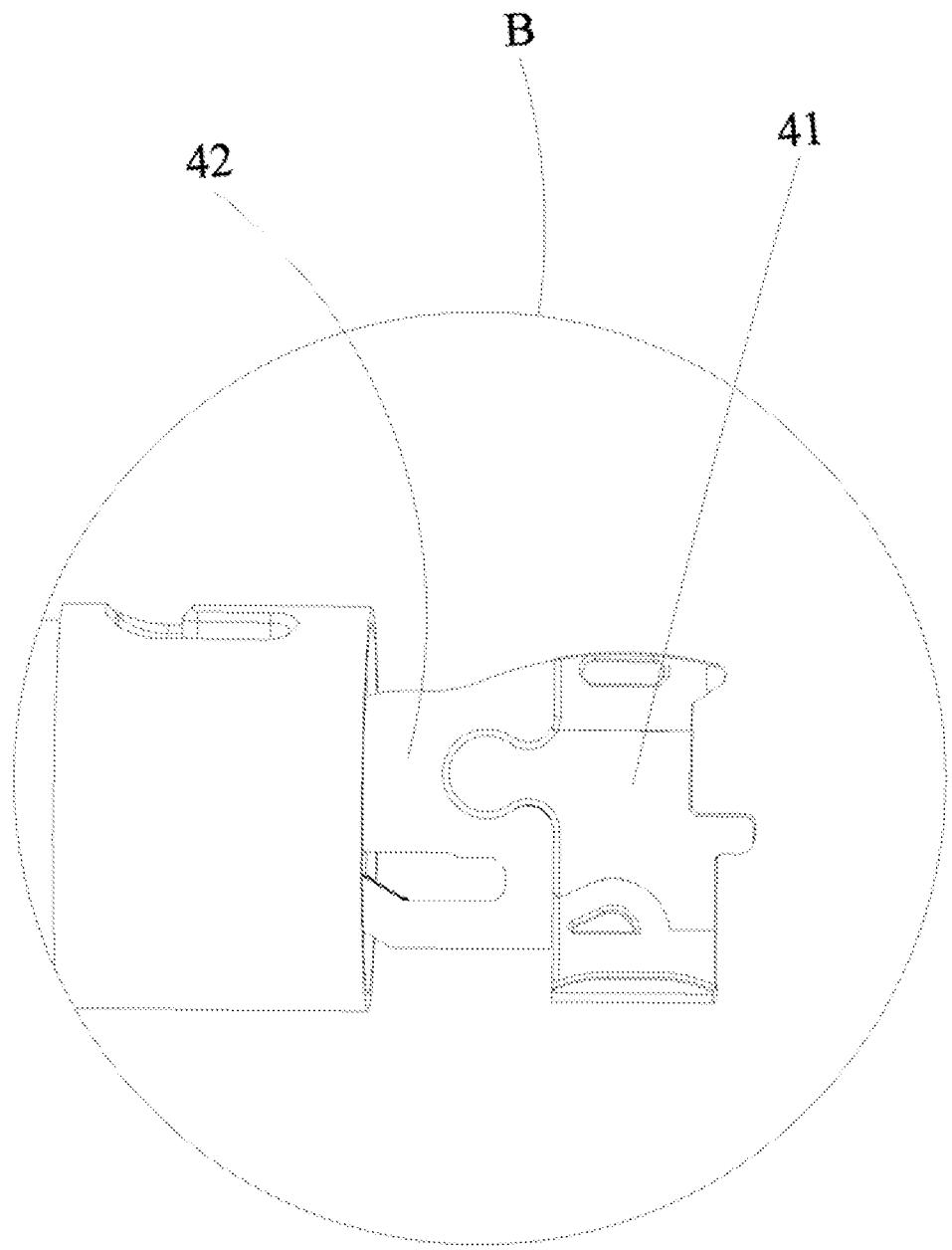
FIG. 5 illustrates an enlarged view of a circled portion B as shown in FIG. 3.
Figure 6:
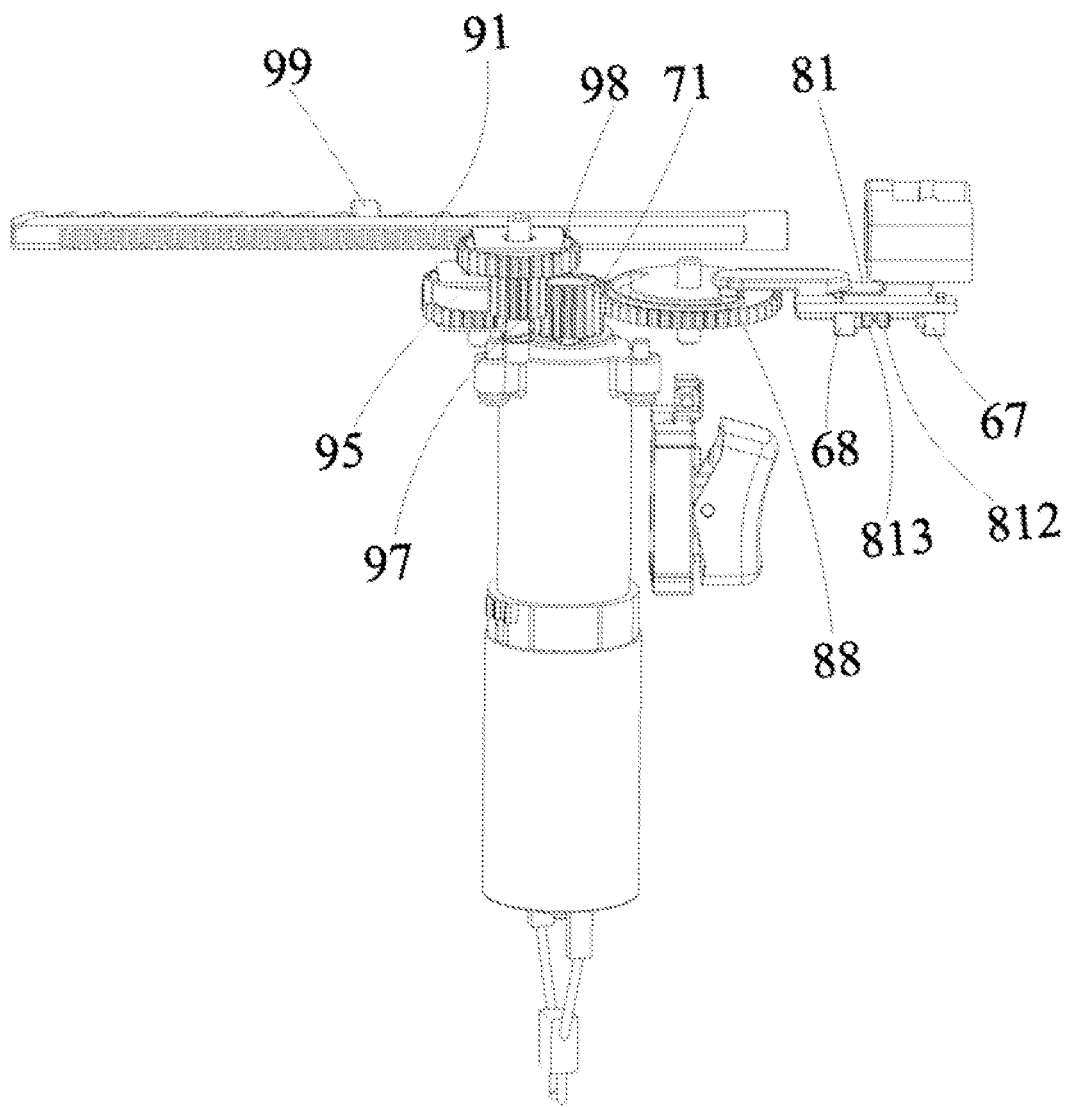
FIG. 6 illustrates a partial schematic diagram of the stapler as shown in FIG. 3.

The stapler 100 further includes a cutting knife assembly 40, the cutting knife assembly 40 includes a cutting knife 41 disposed in the staple cartridge and a knife pushing member 42 detachably connected to the cutting knife 41, a part of the knife pushing member 42 is located in the sleeve 22 and connected to the other end of the mandrel 21, and the other part of the knife pushing member 42 extends into the end effector 30 and is detachably connected to the cutting knife 41. Referring to FIGS. 3 and 5, the knife pushing member 42 is provided with a recess (not labeled), the cutting knife 41 is provided with a protrusion (not labeled), and the recess and the protrusion cooperate to enable the knife pushing member 42 and the cutting knife 41 to be assembled together.

In some embodiments, the stapler 100 further includes a trigger 60, a circuit board assembly 50 and a motor 70. The trigger 60 and the motor 70 are electrically connected to the circuit board assembly 50. The number of the motor 70 is one. The circuit board assembly 50 includes a circuit board 51 and a control module 52 electrically connected to the circuit board 51. The stapler 100 further includes a pressing holding mechanism (not shown in the figure), which is operated by the clinician before the cutting knife assembly 40 is driven to move forwards, and after the pressing holding mechanism finishes working, the clinician may drive the cutting knife assembly 40 to move forwards.

Figure 12:
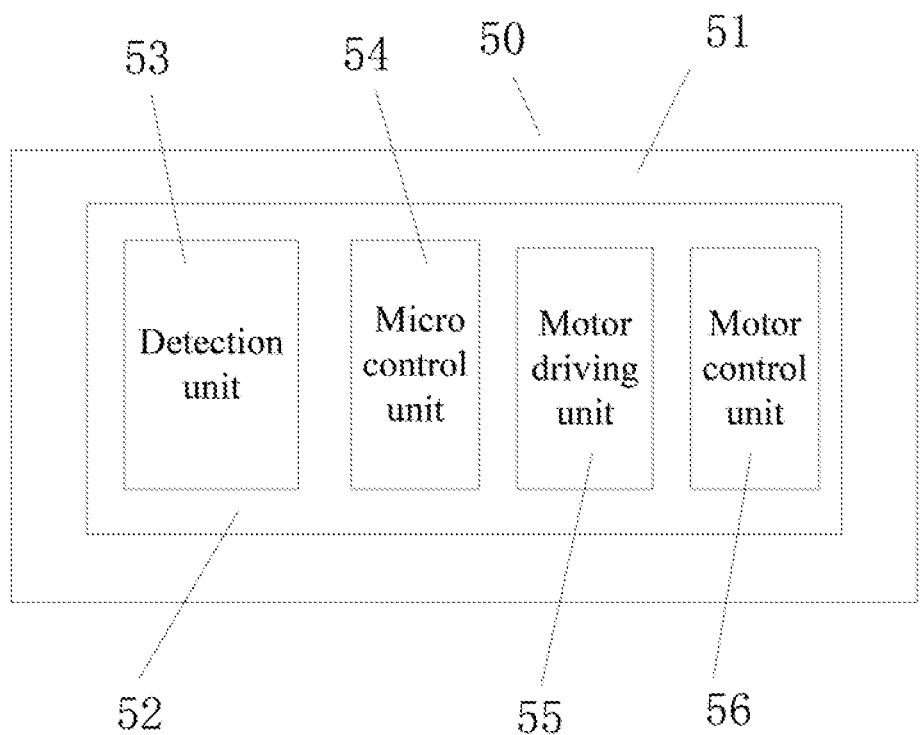
FIG. 12 illustrates a schematic diagram of a circuit board assembly as shown in FIG. 1.

As shown in FIG. 12, in some embodiments, the control module 52 includes a detection unit 53, a micro control unit 54, a motor driving unit 55, and a motor control unit 56. The detecting unit 53 is configured to detect a trigger signal of the trigger 60 and transmit the signal to the micro control unit 54, the micro control unit 54 analyzes and processes the signal and transmits the signal to the motor driving unit 55, the motor driving unit 55 analyzes and processes the signal and transmits the signal to the motor control unit 56, and the motor control unit 56 sends an operation instruction to the motor 70 according to a received signal.

The trigger 60 includes a first button 61 and a second button 62. The first button 61 and the second button 62 are both electrically connected to the control module 52.

The trigger 60 further includes a third button 63 and a fourth button 64, the third button 63 and the fourth button 64 are symmetrically disposed, the third button 63 and the fourth button 64 are both electrically connected to the control module 52, and a same function is achieved no matter which of the third button 63 and the fourth button 64 is pressed by the clinician. In some embodiments, the stapler 100 further includes an indication mechanism (not shown in the figure) electrically connected to the control module 52, the indication mechanism includes five indication lamps, which are LED lamps. The third button 63, the fourth button 64, the control module 52 and the indication mechanism form the pressing holding mechanism together to improve the pressing effect. The clinician presses the third button 63 or the fourth button 64 and releases the same, the control module 52 receives a signal sent by the third button 63 or the fourth button 64 and instructs the indication mechanism to start working, one LED lamp is lighted every three seconds, when all the five LED lamps are in a lighting state, the indication mechanism finishes working, and at the moment, the clinician may operate the first button 61 to drive the cutting knife assembly 40 to move forwards. If the clinician wants to drive the cutting knife assembly 40 to move forwards before the indication mechanism finishes working, to save time, the following operation mode may be used: the third button 63 or the fourth button 64 is pressed and released, the third button 63 or the fourth button 64 is pressed and released again within 15 seconds, and at the moment, the clinician may operate the first button 61 to drive the cutting knife assembly 40 to move forwards. The pressing holding mechanism finishes operation includes: the third button 63 or the fourth button 64 is pressed and released instantly, and the indication mechanism starts to work until the work is finished. The operation of the press holding mechanism is terminated includes: the third button 63 or the fourth button 64 is pressed and released instantly, and the third button 63 or the fourth button 64 is pressed and released again instantly within 15 seconds.

In some embodiments, the trigger 60 further includes a first travel switch 65, a second travel switch 66, a third travel switch 67, and a fourth travel switch 68 electrically connected to the control module 52, the first travel switch 65 is configured to detect whether the cutting knife assembly 40 has moved forwards in place or not, the second travel switch 66 is configured to detect whether the cutting knife assembly 40 has moved backwards in place or not, the third travel switch 67 is configured to detect whether the end effector 30 has been closed in place or not, and the fourth travel switch 68 is configured to detect whether the end effector 30 has been opened in place or not.

The work process of the stapler 100 is as follows: (1) when the clinician presses the first button 61 and keeps a pressing state, the control module 52 receives a signal sent by pressing the first button 61 and then instruct the motor 70 to work, the motor 70 drives the transmission mechanism 11 to work, the transmission mechanism 11 drives the staple abutting seat 32 to pivot downwards so as to close the end effector 30, when the transmission mechanism 11 triggers the third travel switch 67, the control module 52 receives a signal and instructs the motor 70 to stop working, at the moment, the end effector 30 is closed in place, and the clinician releases the first button 61; (2) the clinician operates the pressing holding mechanism; (3) when the pressing holding mechanism finishes operation or the operation of the press holding mechanism is terminated, the clinician presses the first button 61 and keeps a pressing state, the control module 52 receives a signal sent by pressing the first button 61 and then instructs the motor 70 to work, the motor 70 drives the transmission mechanism 11 to work, the transmission mechanism 11 drives the cutting knife assembly 40 to move forwards to cut tissue, when the transmission mechanism 11 triggers the first travel switch 65, the control module 52 receives a signal and instructs the motor 70 to stop working, at the moment, the cutting knife assembly 40 moves forwards in place, and a process of cutting the tissue is finished; (4) the clinician releases the first button 61, the control module 52 receives a signal sent by releasing the first button 61 and instructs the motor 70 to continue to work (retract), the motor 70 drives the transmission mechanism 11 to work, the transmission mechanism 11 drives the cutting knife assembly 40 to move backwards, when the transmission mechanism 11 triggers the second travel switch 66, the control module 52 receives a signal and instructs the motor 70 to stop working, and at the moment, the cutting knife assembly 40 moves backwards in place; (5) the clinician presses the second button 62 and keeps a pressing state, the control module 52 receives a signal sent by pressing the second button 62 and then instructs the motor 70 to work, the motor 70 drives the transmission mechanism 11 to work, the transmission mechanism 11 drives the staple abutting seat 32 to pivot upwards so as to open the end effector 30, when the transmission mechanism 11 triggers the fourth travel switch 68, the control module 52 receives a signal and instructs the motor 70 to stop working, at the moment, the end effector 30 is opened in place, and the clinician releases the second button 62.

The transmission mechanism 11 includes a driving device, the driving device includes a first driving device 80, a second driving device 90 and a fifth gear 71, and the fifth gear 71 is fixed to an output shaft of the motor 70. Or, the fifth gear is fixed to an output shaft of a gearbox driven by the motor 70, i.e., the fifth gear 71 is directly or indirectly connected with the output shaft of the motor 70. The fifth gear 71 is a driving gear, or the fifth gear 71 is referred to as a front driving gear. The fifth gear 71 is always connected with the motor 70 and driven by the motor 70 to rotate, and the connection includes direct connection and indirect connection. In other words, during the work process of the stapler 100, the fifth gear 71 is not disengaged from the motor 70, and the fifth gear 71 is always connected with the motor 70 and driven by the motor 70 to rotate. The first driving device 80 is configured to drive the end effector 30 to be opened and closed, and the second driving device 90 is configured to drive the cutting knife assembly 40 to move forwards and backwards. The motor 70 drives the fifth gear 71 to rotate in a first direction or a second direction, and the first direction is opposite to the second direction. The first driving device 80 and the second driving device 90 are both meshed with the fifth gear 71, and the fifth gear 71 rotates to enable the first driving device 80 or the second driving device 90 to work. When the first driving device 80 works, the first driving device 80 drives the sleeve 22 to move forwards and backwards, thereby pivoting the staple abutting seat 32 to close and open the end effector 30; and when the second driving device 90 works, the second driving device 90 drives the mandrel 21 to move forwards and backwards, thereby enabling the cutting knife assembly 40 to move forwards and backwards. The driving device also includes a rod assembly 20. In some embodiments, the driving device further includes a mandrel 21. In some embodiments, the driving device further includes a sleeve 22.

Figure 8:
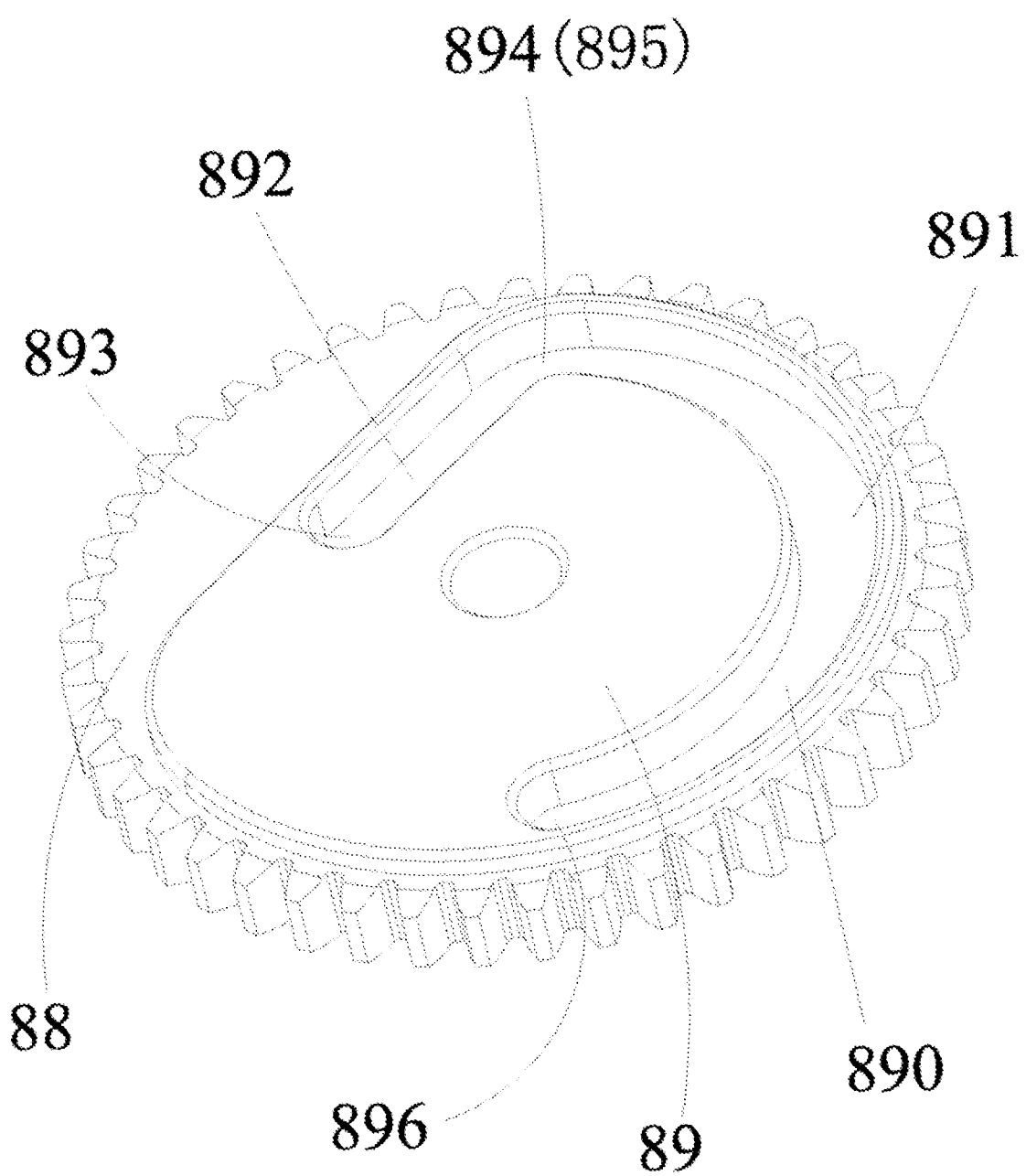
FIG. 8 illustrates a structural schematic diagram of a first gear as shown in FIG. 6.
Figure 9:
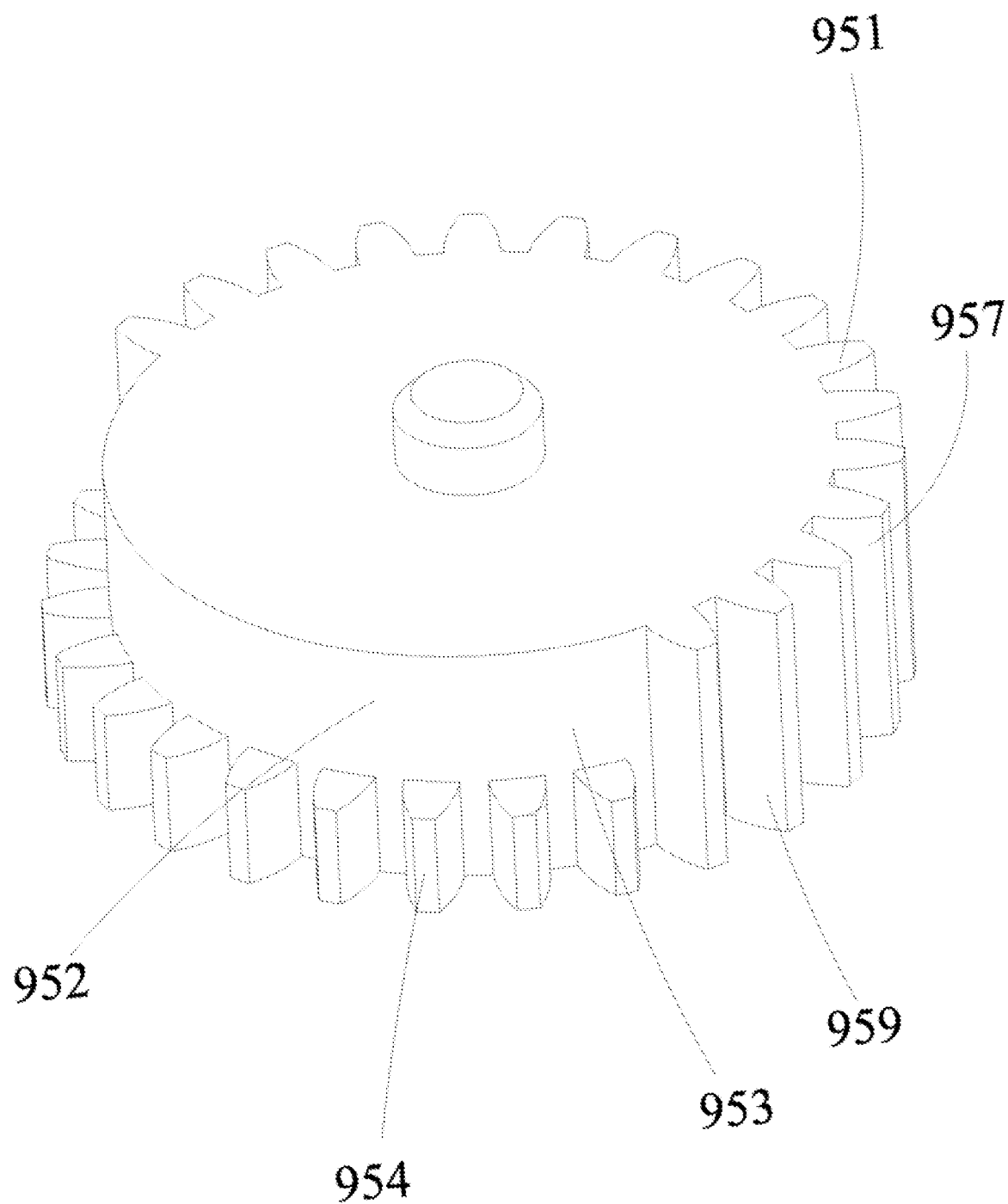
FIG. 9 illustrates a structural schematic diagram of a second gear as shown in FIG. 6.
Figure 13:
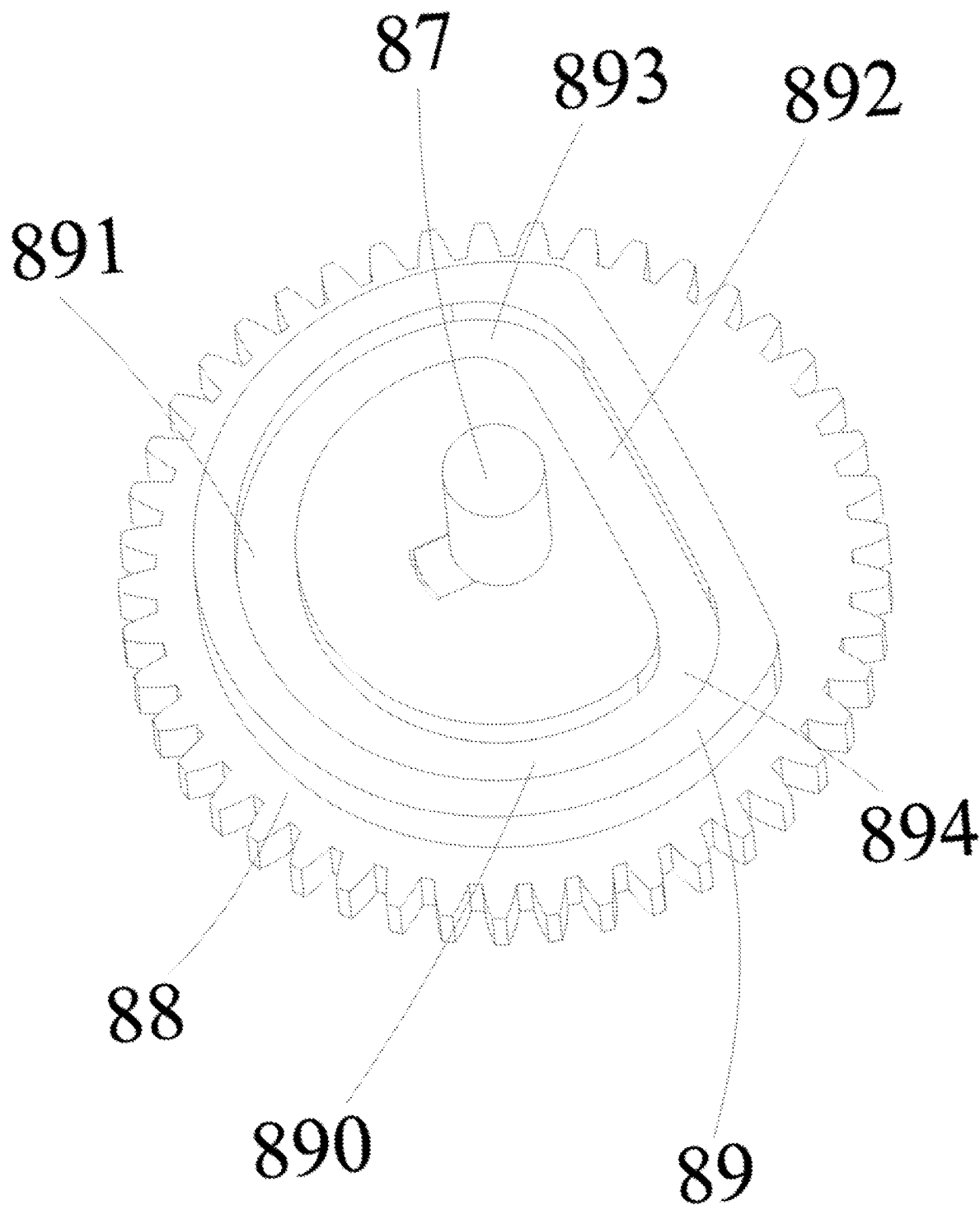
FIG. 13 illustrates a structural schematic diagram of a first gear according to a second embodiment of the disclosure.

In some embodiments, the first driving device 80 includes a compression ring assembly 81 and a first gear assembly 82, the compression ring assembly 81 includes a connecting member 83 and a compression ring 84, the connecting member 83 includes a connecting rod 85 and a protruding column 86 disposed at one end of the connecting rod 85, and the compression ring 84 is disposed at the other end of the connecting rod 85. The first gear assembly 82 includes a first rod 87 and a first gear 88 sleeving the first rod 87, the first rod 87 is fixed to a body (not shown in the figure) of the operation assembly 10, and the first gear 88 rotates around the first rod 87. The first gear 88 includes a cam 89, when the first gear 88 rotates, the cam 89 rotates synchronously, and the first gear 88 is meshed with the fifth gear 71. The cam 89 is provided with a groove 890 formed by sinking downward from a top surface thereof, and the protruding column 86 is located in the groove 890. In some embodiments, the groove 890 includes an arc groove 891 and a straight groove 892, two ends of the straight groove 892 are defined as a first end 893 and a second end 894, respectively, two ends of the arc groove 891 are defined as a third end 895 and a fourth end 896, respectively, and the second end 894 of the straight groove 892 communicates with the third end 895 of the arc groove 891, that is, the second end 894 of the straight groove 892 is substantially the third end 895 of the arc groove 891; 'communicate' means that a part of the groove 890 is through with another part of the groove 890 so that the protruding column 86 may move from a portion of the groove 890 to another portion of the groove 890. Specifically, 'communicate' means that the arc groove 891 is through with the straight groove 892 so that the protruding column 86 may move from the arc groove 891 to the straight groove 892, and the arc groove 891 communicates with the straight groove 892 to form a non-closed groove as shown in FIG. 8, or a closed annular groove as shown in FIG. 13. The first end portion 23 of the sleeve 22 is connected to the compression ring 84, specifically, an outer wall of the first end portion 23 of the sleeve 22 is provided with a groove, an inner wall of the compression ring 84 is provided with a rib 841, the groove and the rib 841 cooperate to assemble the sleeve 22 and the compression ring 84 together, and the second end portion 24 of the sleeve 22 is movably connected to the staple abutting seat 32. When the motor 70 drives the fifth gear 71 to rotate in the first direction, the fifth gear 71 drives the first gear 88 to rotate in the second direction, the cam 89 also rotates synchronously in the second direction, during a rotation of the cam 89, the protruding column 86 moves from the first end 893 of the straight groove 892 to the second end 894 of the straight groove 892 along the straight groove 892, during the process, the compression ring assembly 81 moves forwards, the compression ring assembly 81 drives the sleeve 22 to move forwards, and when the sleeve 22 moves forwards, the second end portion 24 of the sleeve 22 drives the staple abutting seat 32 to rotate downwards for closing; when the motor 70 drives the fifth gear 71 to rotate in the second direction, the fifth gear 71 drives the first gear 88 to rotate in the first direction, the cam 89 also rotates synchronously in the first direction, during the rotation of the cam 89, the protruding column 86 moves from the second end 894 of the straight groove 892 to the first end 893 of the straight groove 892 along the straight groove 892, during the process, the compression ring assembly 81 moves backwards, the compression ring assembly 81 drives the sleeve 22 to move backwards, and when the sleeve 22 moves backwards, the second end portion 24 of the sleeve 22 drives the staple abutting seat 32 to rotate upwards to realize opening. The sleeve 22 is the output member of first gear 88.

When the protruding column 86 is located in the arc groove 891 and moves back and forth along the arc groove 891, since a radial distance from any point of the same inner wall of the arc groove 891 to the first rod 87 is not changed, therefore, when the cam 89 rotates, the distance of the protruding column 86 in a lengthwise direction with respect to the first rod 87 is not changed, that is, the rotation of the cam 89 does not drive the compression ring assembly 81 to move forwards and backwards. Since the radial distance from any point of the same inner wall of the straight groove 892 to the first rod 87 increases in a direction away from the first rod 87 (i.e., in a direction from the first end 893 to the second end 894 in FIG. 8) and decreases in a direction closer to the first rod 87 (i.e., in a direction from the second end 894 to the first end 893 in FIG. 8), therefore, the compression ring assembly 81 is driven to move forwards when the protruding column 86 moves in the straight groove 892 in the direction away from the first rod 87, and the compression ring assembly 81 is driven to move backwards when the protruding column 86 moves in the straight groove 892 in the direction closer to the first rod 87. As shown in FIG. 13, the arc groove 891 communicates with the straight groove 892 to form the closed annular groove, and the portion that functions of the straight groove 892 occupies half of its length. It is to be noted that the movement of the protruding column 86 in the groove 890 is a relative movement, which is achieved by the rotation of the cam 89.

In some embodiments, the second driving device 90 includes a rack 91, a second gear assembly 92, and a third gear assembly 93. The second gear assembly 92 includes a second rod 94 and a second gear 95 sleeving the second rod 94, the second rod 94 is fixed to the body of the operation assembly 10, the second gear 95 rotates around the second rod 94, and the second gear 95 is meshed with the fifth gear 71; and the second gear 95 includes a first toothed portion 951 and a tooth-missing portion 952 that are disposed adjacently in a circumferential direction, the first toothed portion 951 and the tooth-missing portion 952 have a first boundary and a second boundary therebetween, and the tooth-missing portion 952 includes a non-toothed portion 953 and a second toothed portion 954 that are disposed adjacently in the vertical direction (i.e., the axial direction). The second gear 95 is always kept meshed with the fifth gear 71 by the first toothed portion 951 and the second toothed portion 954. The third gear assembly 93 includes a third rod 96, a third gear 97 and a fourth gear 98 sleeving the third rod 96, the third rod 96 is fixed to the body of the operation assembly 10, the third gear 97 and the fourth gear 98 rotate around the third rod 96, the third gear 97 and the fourth gear 98 are integrally formed, the third gear 97 and the fourth gear 98 have different diameters, the third gear 97 is configured to be meshed with a portion, parallel to the non-toothed portion 953, of the first toothed portion 951 of the second gear 95, and the fourth gear 98 is meshed with the rack 91. The rack 91 is the output member of the second gear 95, and a diameter of the fourth gear 98 is greater than a diameter of the third gear 97.

Since the fifth gear 71 connected to the output shaft of the motor 70 has a first rotation speed, but the movement of the rack 91 requires a second speed, in order to convert the first rotation speed of the fifth gear 71 into the second speed of the movement of the rack 91, the third gear 97 and a fourth gear 98 need to be disposed between the fifth gear 71 and the rack 91 for adjustment. Since the diameters of the third gear 97 and the fourth gear 98 are different, linear speeds at which the third gear 97 and the fourth gear 98 rotate are also different, and thus, the third gear 97 and the fourth gear 98 may convert the first rotation speed of the fifth gear 71 into the second speed of the movement of the rack 91.

The working process of the stapler 100 will be described in detail below.

An operator presses the first button 61 and keeps the pressing state, the control module 52 receives a signal generated by pressing the first button 61 and sends an operation instruction to the motor 70, the motor 70 drives the fifth gear 71 to rotate in the first direction, the fifth gear 71 drives the first gear 88 to rotate in the second direction, the cam 89 also synchronously rotates in the second direction, during the rotation of the cam 89, the protruding column 86 of the compression ring assembly 81 moves from the first end 893 of the straight groove 892 to the second end 894 of the straight groove 892 (i.e. the third end 895 of the arc groove 891) along the straight groove 892, so that the compression ring assembly 81 is driven to move forwards, the compression ring assembly 81 drives the sleeve 22 to move forwards, and at the moment, the sleeve 22 drives the staple abutting seat 32 to rotate downwards to further close the end effector 30; on the other hand, during the process that the protruding column 86 moves from the first end 893 of the straight groove 892 to the second end 894 of the straight groove 892 along the straight groove 892, the fifth gear 71 drives the second gear 95 to rotate in the second direction, during the process, an intersection position of the second gear 95 and the third gear 97 is at the non-toothed portion of the second gear 95, so that the rotation of the second gear 95 does not drive the third gear 97 to rotate, thereby allowing the cutting knife 41 to remain stationary during the closing of the end effector 30.

When the compression ring assembly 81 advances to a certain position, a first tab 812 on the compression ring assembly 81 triggers the third travel switch 67 at a front stop point of the forward movement of the compression ring assembly 81, i.e., the end effector 30 is closed in place, and at the moment, the protruding column 86 is located at the second end 894 of the straight groove 892 (i.e., the third end 895 of the arc groove 891). The control module 52 receives a signal sent by the third travel switch 67 and sends an instruction of stopping operation to the motor 70, and the motor 70 stops rotating. The clinician does not hear a sound of the operation of the motor 70 and releases the first button 61 and operates the pressing holding mechanism.

After the pressing holding mechanism finishes working or the operation of the pressing holding mechanism is terminated, the clinician presses the first button 61 and keeps the pressing state, the control module 52 receives a signal generated by pressing the first button 61 and analyzes the signal, the control module 52 generates an operation instruction to the motor 70 according to the analyzed signal, the motor 70 drives the fifth gear 71 to continue to rotate in the first direction, the fifth gear 71 drives the second gear 95 to rotate in the second direction, the intersection position of the second gear 95 and the third gear 97 is rotated to the portion, parallel to the non-toothed portion 953, of the first toothed portion 951 from the non-toothed portion 953 of the second gear 95, the first toothed portion 951 of the second gear 95 is meshed with the third gear 97 and drives the third gear 97 to rotate in the first direction, the fourth gear 98 also rotates in the first direction due to the fact that the third gear 97 and the fourth gear 98 are integrally formed, the fourth gear 98 drives the rack 91 to move forwards, the rack 91 drives the mandrel 21 to move forwards, the mandrel 21 drives the knife pushing member 42 to move forwards, and the knife pushing member 42 drives the cutting knife 41 to move forwards to cut tissue; on the other hand, the fifth gear 71 drives the first gear 88 to rotate in the second direction, the protruding column 86 moves from the second end 894 of the straight groove 892 (i.e., the third end 895 of the arc groove 891) to the fourth end 896 of the arc groove 891 along the arc groove 891, at the moment, the rotation of the cam 89 does not drive the compression ring assembly 81 to move forwards and backwards, thereby allowing the end effector 30 to remain closed during the forward movement of the cutting knife 41.

When the rack 91 advances to a certain position, the protruding portion 99 on the rack 91 contacts with the first travel switch 65, a position of the first travel switch 65 is the front stop point of the forward movement of the cutting knife 41, namely the position of cutting completion, and at the moment, the protruding column 86 is located at the fourth end 896 of the arc groove 891; the meshing point of the second gear 95 and the third gear 97 is located close to the first boundary of the first toothed portion 951 and the tooth-missing portion 952 of the second gear 95, that is, if the second gear 95 continues to rotate in the second direction, the first toothed portion 951 of the second gear 95 will be disengaged from the third gear 97. The control module 52 receives a signal generated by the first travel switch 65 and sends an instruction of stopping operation to the motor 70, the motor 70 stops rotating, the clinician releases the first button 61, the control module receives a signal generated by releasing the first button 61 and sends an operation instruction to the motor 70, the motor drives the fifth gear 71 to rotate in the second direction, the fifth gear 71 drives the second gear 95 to rotate in the first direction, the first toothed portion 951 of the second gear 95 drives the third gear 97 to rotate in the second direction, the fourth gear 98 also rotates in the second direction due to the fact that the third gear 97 and the fourth gear 98 are integrally formed, the fourth gear 98 drives the rack 91 to move backwards, the rack 91 drives the mandrel 21 to move backwards, the mandrel 21 drives the knife pushing member 42 to move backwards, and the knife pushing member 42 drives the cutting knife 41 to move backwards, so that retracting is realized; and on the other hand, the fifth gear 71 drives the first gear 88 to rotate in the first direction, the protruding column 86 moves from the fourth end 896 of the arc groove 891 to the third end 895 of the arc groove 891 (i.e., the second end 894 of the straight groove 892) along the arc groove 891, and at the moment, the rotation of the cam 89 does not drive the compression ring assembly 81 to move forwards and backwards, thereby allowing the end effector 30 to remain closed during the backward movement of the cutting knife 41.

When the rack 91 moves backwards to a certain position, the protruding portion 99 on the rack 91 contacts with the second travel switch 66, the position of the second travel switch 66 is a rear stop point of the backward movement of the cutting knife 41, and at the moment, the protruding column 86 is located at the third end 895 of the arc groove 891 (i.e., the second end 894 of the straight groove 892); and the meshing point of the second gear 95 and the third gear 97 is located close to the second boundary of the first toothed portion 951 and the tooth-missing portion 952 of the second gear 95, that is, if the second gear 95 continues to rotate in the first direction, the first toothed portion 951 of the second gear 95 will be disengaged from the third gear 97. The control module 52 receives a signal sent by the second travel switch 66 and sends an instruction of stopping operation to the motor 70, at the moment, the motor 70 stops working, and retracting is finished. After retracting is finished, the clinician presses the second button 62 and keeps the pressing state, the control module 52 receives a signal generated by pressing the second button 62 and sends an operation instruction to the motor 70, the motor 70 drives the fifth gear 71 to rotate in the second direction, the fifth gear 71 drives the first gear 88 to rotate in the first direction, the cam 89 also synchronously rotates in the first direction, during the rotation of the cam 89, the protruding column 86 moves from the second end 894 of the straight groove 892 to the first end 893 of the straight groove 892 along the straight groove 892, the compression ring assembly 81 moves backwards, the compression ring assembly 81 drives the sleeve 22 to move backwards, and at the moment, the sleeve 22 drives the staple abutting seat 32 to rotate upwards to further open the end effector 30; and on the other hand, the fifth gear 71 drives the second gear 95 to rotate in the first direction, the first toothed portion 951 of the second gear 95 is disengaged from the third gear 97, namely, in the process that the protruding column 86 moves from the second end 894 of the straight groove 892 to the first end 893 of the straight groove 892 along the straight groove 892, the boundary of the second gear 95 and the third gear 97 is located at the non-toothed portion 953 of the second gear 95, so that the rotation of the second gear 95 does not drive the third gear 97 to rotate, thereby allowing the cutting knife 41 to remain stationary during an opening process of the end effector 30.

When the compression ring assembly 81 retreats to a certain position, a second tab 813 on the compression ring assembly 81 contacts with the fourth travel switch 68 at the rear stop point of the backward movement of the compression ring assembly 81, i.e., the end effector 30 is opened in place, and at the moment, the protruding column 86 is located at the first end 893 of the straight groove 892. The control module 52 receives a signal sent by the fourth travel switch 68 and sends an instruction of stopping operation to the motor 70, and at the moment, the motor 70 stops working.

Figure 7:
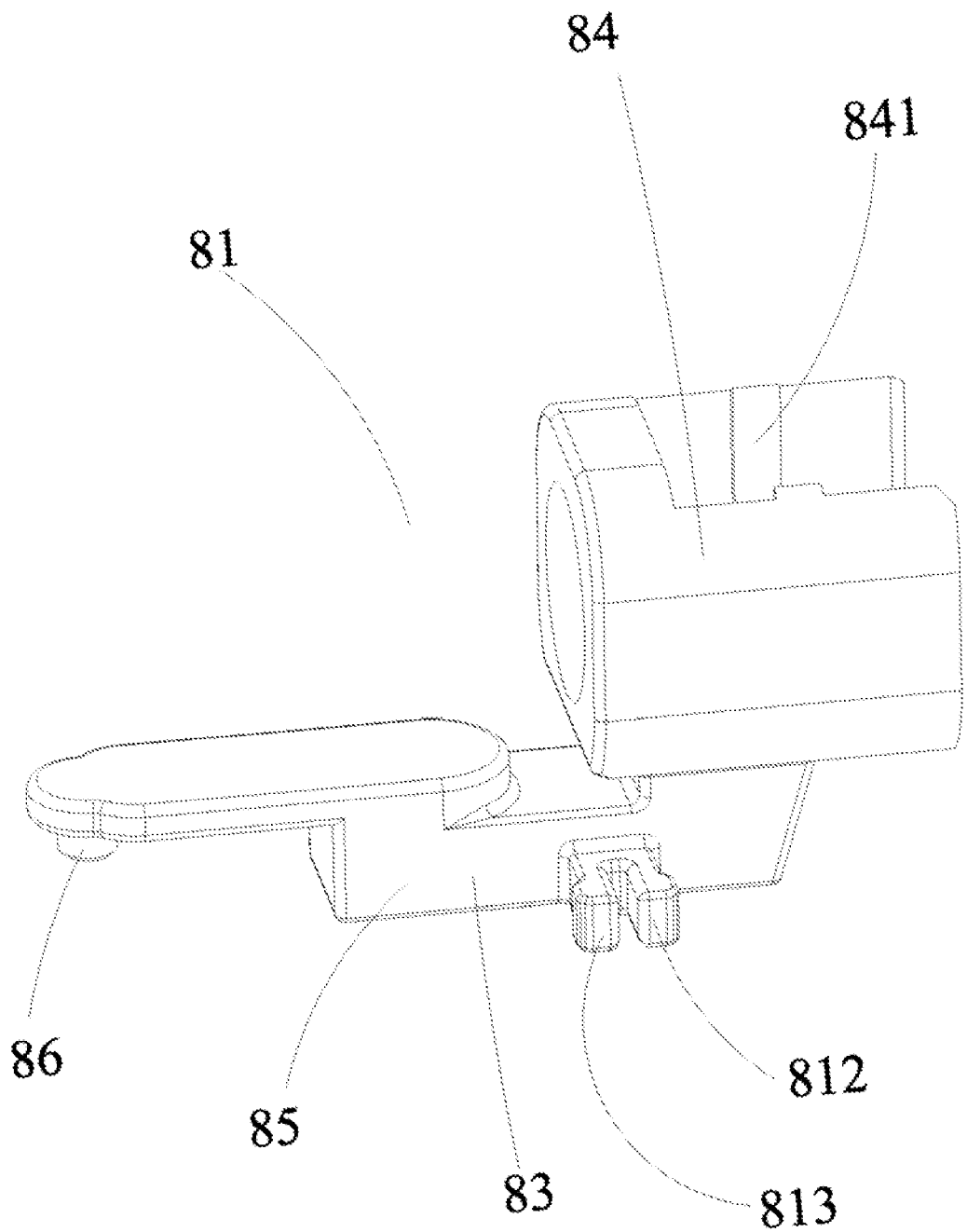
FIG. 7 illustrates a structural schematic diagram of a compression ring assembly as shown in FIG. 6.
Figure 14:
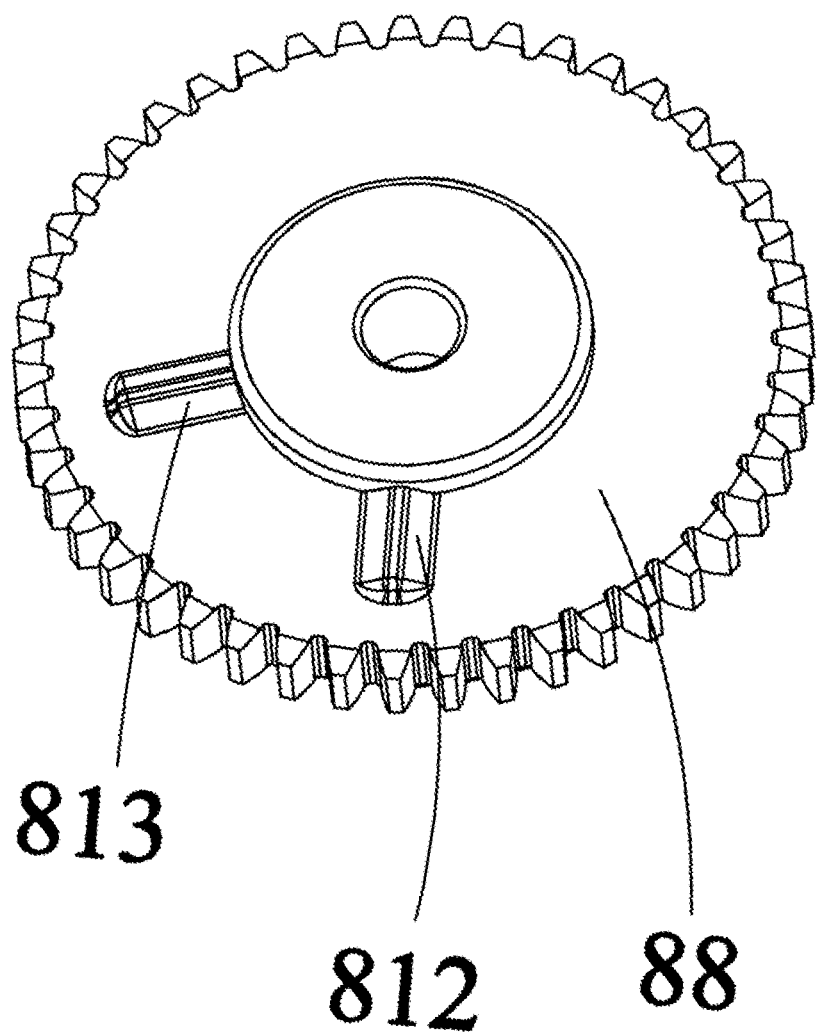
FIG. 14 illustrates a structural schematic diagram of a first gear according to another embodiment of the disclosure.

In the embodiment, the first tab 812 and the second tab 813 are disposed on the compression ring 84, or disposed on the connecting rod 85, as shown in FIG. 7. In other embodiments, the first tab 812 and the second tab 813 may also be disposed on the first gear 88, as shown in FIG. 14.

In the embodiment, the first gear 88 includes an effective stroke structure and an idle stroke structure, the first gear 88 includes the arc groove 891 and the straight groove 892, the straight groove 892 is the effective stroke structure, and the arc groove 891 is the idle stroke structure. When the protruding column 86 moves in the straight groove 892, the first gear 88 drives the compression ring assembly 81 to move forwards; and when the protruding column 86 moves in the arc groove 891, the first gear 88 does not drive the compression ring assembly 81 to move forwards. The second gear 95 includes an effective stroke structure and an idle stroke structure, the second gear 95 includes the first toothed portion 951 and the tooth-missing portion 952, the tooth-missing portion 952 includes the second toothed portion 954 and the non-toothed portion 953, the non-toothed portion 953 is the idle stroke structure, and a portion, parallel to the non-toothed portion 953, of the first toothed portion 951 is the effective stroke structure. When the third gear 97 is meshed with the portion, parallel to the non-toothed portion 953, of the first toothed portion 951 of the second gear 95, the second gear 95 drives the third gear 97 to move; and when the third gear 97 is meshed with the non-toothed portion 953 of the second gear 95, the second gear 95 does not drive the third gear 97 to move.

As can be seen, in the embodiment, the tooth-missing portion 952 includes the second toothed portion 954 and the non-toothed portion 953 which are disposed adjacently in a vertical direction (axial direction). Although the first toothed portion 951 is disposed integrally, the first toothed portion 951 includes a first tooth portion 959 and a second tooth portion 957 which are different in meshing targets in the vertical direction (axial direction): the first tooth portion 959 is always meshed with the fifth gear 71, and the second tooth portion 957 is selectively meshed with the third gear 97. The first tooth portion 959 and the second tooth portion 957 are disposed adjacently in the vertical direction, and the boundary of the first tooth portion 959 and the second tooth portion 957 is located at the same height as the boundary of the second toothed portion 954 and the non-toothed portion 953.

The first tooth portion 959 and the second toothed portion 954 are disposed adjacently in the circumferential direction. The first tooth portion 959 and the second toothed portion 954 are equal in height. A top surface (virtual surface) of the first tooth portion 959 is located at the same height as a top surface of the second toothed portion 954. In the circumferential direction, the first tooth portion 959 and the second toothed portion 954 form a complete gear, which is named a sixth gear for convenience of description, and the sixth gear is always meshed with the fifth gear 71 and is driven to rotate by the fifth gear 71. The second tooth portion 957 and the non-toothed portion 953 are disposed adjacently in the circumferential direction. The second toothed portion 957 and the non-toothed portion 953 are equal in height. A bottom surface (virtual surface, the same as the top surface of the first tooth portion 959) of the second tooth portion 957 is located at the same height as a bottom surface (the same as the top surface of the second toothed portion 954) of the non-toothed portion 953. The second toothed portion 957 is an effective stroke structure, and the non-toothed portion 953 is an idle stroke structure. The sixth gear forms a driving gear of the second tooth portion 957. The sixth gear is driven by the fifth gear 71 to rotate, when the sixth gear rotates to enable the second tooth portion 957 of the first toothed portion 951 to be meshed with the third gear 97, the fifth gear 71 sequentially drives the second tooth portion 957, the third gear 97 and the fourth gear 98 to rotate through the sixth gear, so that the rack 91 is driven to linearly move; and when the sixth gear rotates to couple the non-toothed portion 953 and the third gear 97, the fifth gear 71 and the sixth gear may rotate under the driving of the motor 70, but the third gear 97 and the fourth gear 98 do not rotate, and the rack 91 does not output linear movement. 'Coupling' means that a part of teeth of the third gear 97 is located in a spatial region where the non-toothed portion 953 is located without contacting with the non-toothed portion 953, and the third gear 97 is not driven in the process of coupling with the non-toothed portion 953 since there is no contact with the non-toothed portion 953 (including not meshing due to fact that the non-toothed portion 953 has no teeth).

In some embodiments of the disclosure, the idle stroke means that the driving device has no motion output, i.e., does not drive the cutting knife or the end effector, when the driving device has motion input, i.e., is driven. The idle stroke structure is a structure that is included in a component of the driving device and that may realize the idle stroke. Effective stroke means that the driving device has motion output, i.e., drives the cutting knife or the end effector, when the driving device has motion input, i.e., is driven. The effective stroke structure is a structure that is included in a component of the driving device and that may realize the effective stroke.

The driving device includes a driving gear, in the embodiment, the fifth gear 71 is the driving gear, the driving gear is always connected with the motor 70 and is driven by the motor 70, and the motor 70 drives the first driving device 80 and the second driving device 90 by the driving gear (the fifth gear 71). Or the fifth gear is referred to as a front driving gear.

The first driving device 80 includes a first driving gear driven by the motor 70. In some embodiments, the motor 70 drives the first driving gear by the front driving gear. In the embodiment, the first driving gear is the first gear 88. The first driving device 80 further includes a first effective stroke structure (straight groove 892) and a first idle stroke structure (arc groove 891). In some embodiments, the first effective stroke structure (straight groove 892) and the first idle stroke structure (arc groove 891) are disposed on the end face of the first gear 88. The first driving device 80 also includes a first output member, which in the embodiment is the sleeve 22.

Thus, when the front driving gear drives the first effective stroke structure by the first driving gear of the first driving device 80, the first output member is driven by the first effective stroke structure to move, and when the front driving gear drives the first idle stroke structure by the first driving gear of the first driving device 80, the first output member is not driven by the first idle stroke structure and does not move. In some embodiments, when the fifth gear 71 drives the first effective stroke structure (straight groove 892) by the first gear 88 of the first driving device 80, the sleeve 22 is driven by the first effective stroke structure to move, and when the fifth gear 71 drives the first idle stroke structure (arc groove 891) by the first gear 88 of the first driving device 80, the sleeve 22 is not driven by the first idle stroke structure and does not move.

The second driving device 90 includes a second driving gear driven by the motor 70. In some embodiments, the motor drives the second driving gear by the front driving gear. In the embodiment, the second driving gear is a sixth gear formed by the first tooth portion 959 and the second toothed portion 954 of the second gear 95. The second driving device 90 further includes a second effective stoke structure (the second tooth portion 957, disposed adjacent to the non-toothed portion 953, of the first toothed portion 951) and a second idle stoke structure (the non-toothed portion 953). The second driving device 90 also includes a second output member, which in the embodiment is the rack 91.

Thus, when the front driving gear drives the second effective stroke structure by the second driving gear of the second driving device 90, the rack linearly moves, and when the front driving gear drives the second idle stroke structure by the second driving gear of the second driving device 90, the rack 91 does not move. Specifically, when the fifth gear 71 drives the second tooth portion 957 by the sixth gear, the rack 91 linearly moves; and when the fifth gear 71 drives the non-toothed portion 953 by the sixth gear, the rack does not move.

That is, one driving gear (the fifth gear 71) may drive the sleeve 22 to move through the first driving device 80 including the first effective stroke structure (the straight groove 892), and also may drive the rack 91 to move through the second driving device 90 including the second effective stroke structure (the second tooth portion 957), and the structural design is quite reasonable. In some embodiments, the movement of the sleeve 22 and the movement of the rack 91 are both linear movements.

The fifth gear 71 is always connected with the motor 70 and driven by the motor 70, the fifth gear 71 rotates as long as the motor 70 is started to rotate a motor shaft, and the sleeve 22 is not driven by the first driving device 80 and the rack 91 is not driven by the second driving device 90 to move simultaneously in the rotation process of the fifth gear 71, so that an incorrect use of the stapler may be avoided. In some embodiments, the motor 70 alternatively drives one of the first effective stroke structure and the second effective stroke structure. That is, during driving, the motor 70 may only drive one of the first effective stroke structure and the second effective stroke structure. Therefore, the motor 70 does not drive the rack 91 when driving the sleeve 22, and does not drive the sleeve 22 when driving the rack 91, so that the stapler works reasonably.

The driving device has two states: in the first state, the motor 70 drives the first effective stroke structure and the second idle stroke structure; and in the second state, the motor 70 drives the second effective stroke structure and first idle stroke structure.

That is, in the first state, the driving gear (the fifth gear 71) drives the first effective stroke structure of the first driving device 80 and the second idle stroke structure of the second driving device 90, so that the driving gear does not drive the rack 91 to move when driving the sleeve 22 to move, and the driving gear (the fifth gear 71) does not drive the cutting knife assembly 40 to move while driving the end effector 30 to be opened or closed.

In the second state, the driving gear (the fifth gear 71) drives the second effective stroke structure of the second driving device 90 and the first idle stroke structure of the first driving device 80, so that the driving gear (the fifth gear 71) does not drive the sleeve 22 to move when driving the cutting knife assembly 40 to move, and the driving gear (the fifth gear 71) does not drive the end effector 40 to be opened or closed while driving the cutting knife assembly 30 to move.

It can be seen that the driving gear (the fifth gear 71) may drive both the first driving device 80 and the second driving device 90, but the driving gear does not drive both the first effective stroke structure of the first driving device 80 and the second effective stroke structure of the second driving device 90, and the design is quite reasonable. Meanwhile, the two states of the driving device satisfy the logic of action of the end effector 30 and the cutting knife assembly 40.

As can be seen, the groove 890 of the cam 89 includes the arc groove 891 and the straight groove 892, the protruding column 86 is located in the groove 890, so that the end effector 30 may be driven to be opened and closed, and meanwhile, the end effector 30 may remain closed during movement of the cutting knife assembly 40. The second gear 95 includes the first toothed portion 951 and the tooth-missing portion 952, the first toothed portion 951 includes the second tooth portion 957, and the tooth-missing portion 952 includes the non-toothed portion 953, thereby driving the cutting knife assembly 40 to move forwards and backwards and allowing the cutting knife assembly 40 to remain stationary during opening and closing of the end effector 30. The stapler 100 of the disclosure is provided with one motor 70 that may drive the first driving work 80 to work, thereby driving the end effector 30 to be opened and closed, and also may drive the second driving device 90 to work, thereby driving the cutting knife assembly 40 to move forwards and backwards; and meanwhile, the logic of action between the end effector 30 and the cutting knife assembly 40 is satisfied. In some embodiments, in the process that the motor 70 drives the driving device to work, the effective stroke and the idle stroke are realized by the structure of the components of the driving device, a relative position between the components of the driving device for realizing the effective stroke and the idle stroke does not need to be changed, the relative position does not need to be changed, means that the protruding column is always located in the groove and there is no relative linear displacement between the second gear and the third gear, the structure and the interconnection relationship of the components are simple, the probability of generating assembly errors is small in the process of assembling the components, and the stapler 100 is not prone to malfunction in the working process.

In a second embodiment, the first gear may be replaced with a first gear as shown in FIG. 13, the first gear 88 includes a cam 89, the cam 89 is provided with a groove 890 formed by sinking downward from the top surface thereof, and the protruding column 86 of the connecting member 83 is located in the groove 890. The groove 890 includes an arc groove 891 and a straight groove 892, two ends of the arc groove 891 communicate through the straight groove 892, that is, the straight groove 892 and the arc groove 891 form a closed ring together; 'communicate' means that a part of the groove 890 is through with another part of the groove 890 so that the protruding column 86 may move from a part of the groove 890 to another part of the groove 890; and two ends of the straight groove 892 are defined as a first end 893 and a second end 894, respectively, and the intermediate position between the first end 893 and the second end 894 is a middle. During the rotation of the cam 89, the protruding column 86 moves from the middle of the straight groove 892 to the second end 894 of the straight groove 892 along the straight groove 892, during the process, the compression ring assembly 81 moves forwards, the compression ring assembly 81 drives the sleeve 22 to move forwards, and when the sleeve 22 moves forwards, the second end portion 24 of the sleeve 22 drives the staple abutting seat 32 to rotate downwards for realizing closing; and during the rotation of the cam 89, the protruding column 86 moves from the second end 894 of the straight groove 892 to the middle of the straight groove 892 along the straight groove 892, during the process, the compression ring assembly 81 moves backwards, the compression ring assembly 81 drives the sleeve 22 to move backwards, and when the sleeve 22 moves backwards, the second end portion 24 of the sleeve 22 drives the staple abutting seat 32 to rotate upwards for realizing opening. When the protruding column 86 is located in the arc groove 891 and moves back and forth along the arc groove 891, since the radial distance from any point of the same inner wall of the arc groove 891 to the first rod 87 is not changed, when the cam 89 rotates, the distance of the protruding column 86 in the lengthwise direction with respect to the first rod 87 is not changed, that is, the rotation of the cam 89 does not drive the compression ring assembly 81 to move forwards and backwards. In the embodiment, the protruding column 86 moves from the middle of straight groove 892 to the second end 894 (one end of the arc groove) of the straight groove 892 along the straight groove 892, thereby realizing closing of the end effector 30; the protruding column 86 then moves from the second end 894 of the straight groove 892 to the first end 893 of the straight groove 892 (the other end of the arc groove 891) along the arc groove 891, thereby allowing the end effector 30 to remain closed during the process of forward movement of the cutting knife 41; and the protruding column 86 moves from the first end 893 of the straight groove 892 to the second end 894 of the straight groove 892 along the arc groove 891, thereby allowing the end effector 30 to remain closed during the process of backward movement of the cutting knife 41; and the protruding column 86 moves from second end 894 of the straight groove 892 to the middle of the straight groove 892 along the straight groove 892, thereby allowing the end effector 30 to be opened.

FIGS. 21-28 illustrate a surgical instrument according to a third embodiment of the disclosure.

Figure 21:
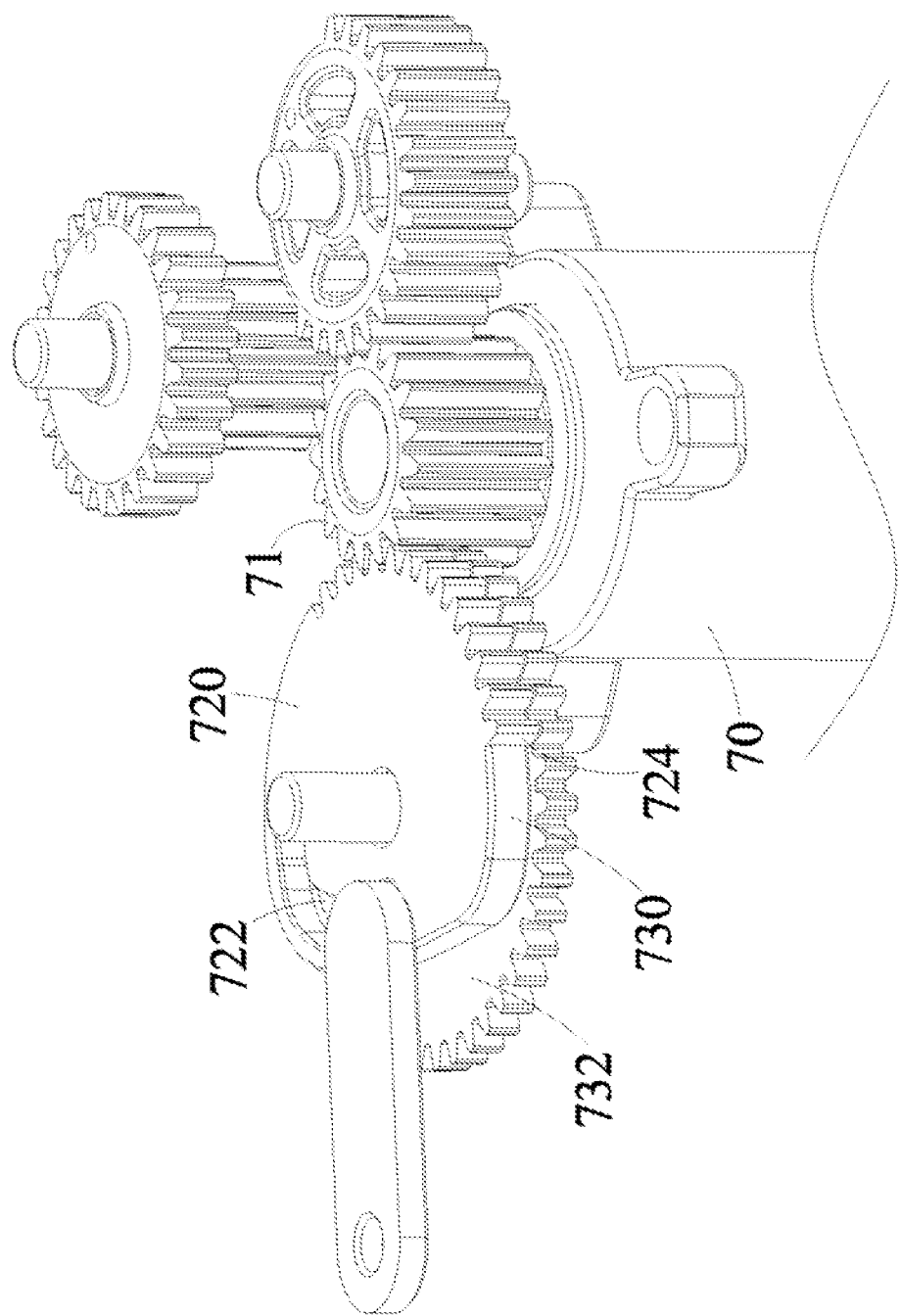
FIG. 21 illustrates a partial structural schematic diagram of a stapler according to a third embodiment of the disclosure.
Figure 22:
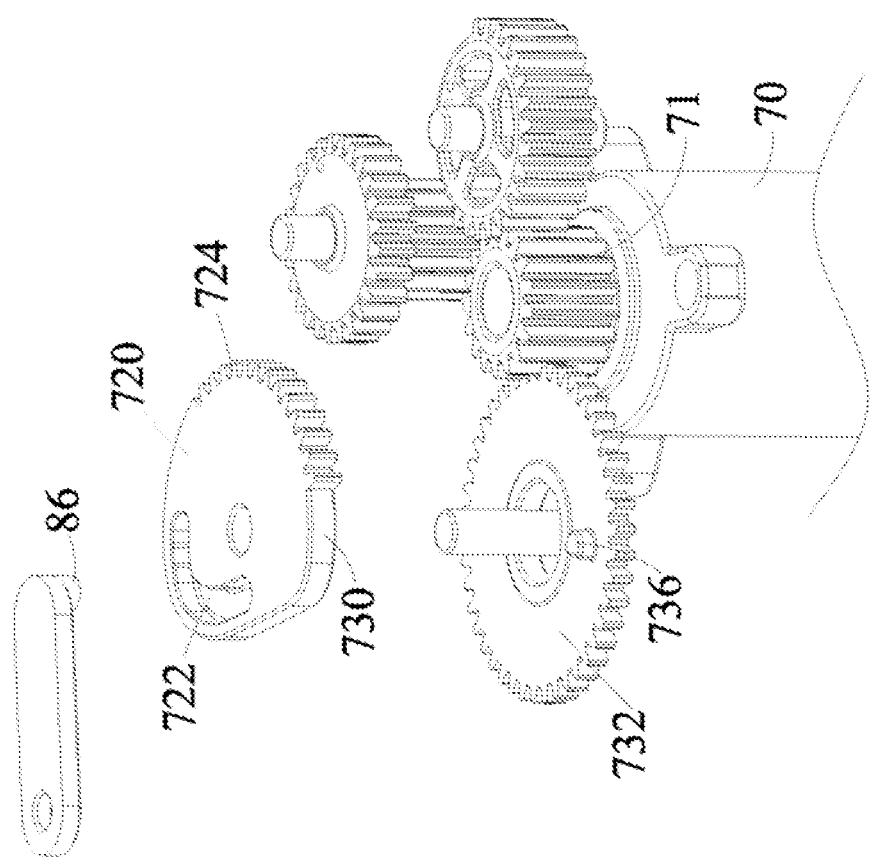
FIG. 22 illustrates a partial perspective exploded view of the stapler as shown in FIG. 21.
Figure 23:
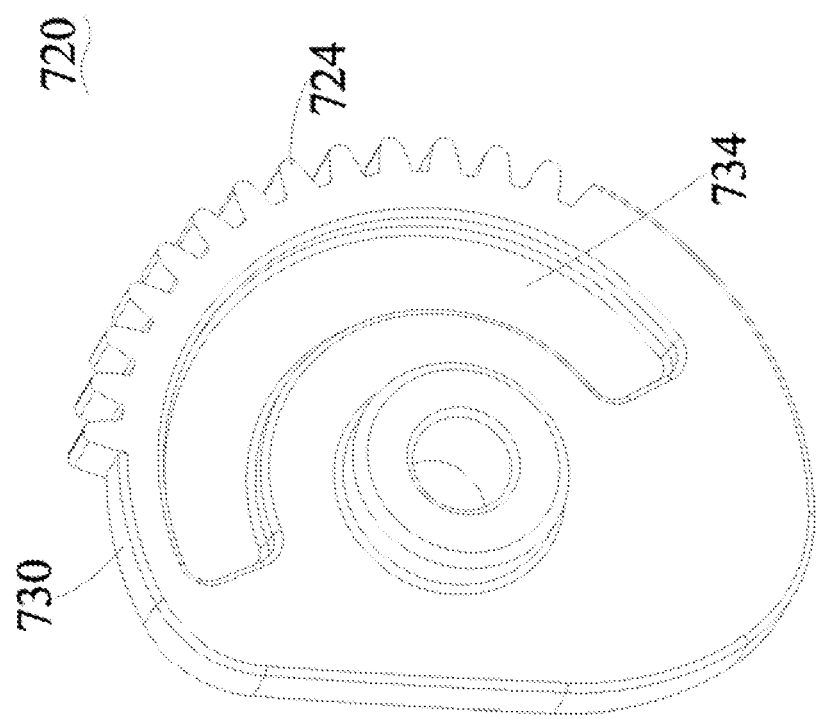
FIG. 23 illustrates a perspective view of a rotating member of the stapler as shown in FIG. 22.

Referring to FIGS. 21-23, the embodiment relates to a surgical instrument, in particular to a stapler, similar to the first embodiment.

Similar to the first embodiment, the surgical instrument includes a driving assembly (a motor 70 and a fifth gear 71 driven by the motor 70), an end effector and a cutting knife assembly driven by the driving assembly through a driving device. The driving device includes a first driving device and a second driving device. The first driving device drives the end effector, and the second driving device drives the cutting knife assembly. Thus, the first driving device is referred to as the end effector driving device, and the second driving device is referred to as the cutting knife assembly driving device.

Similar to the first embodiment, the first driving device includes a first effective stroke structure and a first idle stroke structure. The second driving device includes a second effective stroke structure and a second idle stroke structure. The motor 70 alternatively drives one of the first effective stroke structure and the second effective stroke structure. That is, during use of the surgical instrument, the motor 70 either drives the first effective stroke structure, thereby driving the end effector to be opened or closed, or the second effective stroke structure, thereby driving the cutting knife assembly to move forwards (advance) or backwards (retract), and errors in the working process of the stapler are avoided.

In some embodiments, the driving device has two states: in a first work state, the motor 70 drives the first effective stroke structure and is coupled with the second idle stroke structure; and in a second work state, the motor 70 drives the second effective stroke structure and is coupled with the first idle stroke structure. That is, in the first work state, the motor 70 drives the end effector to be opened or closed without driving the cutting knife assembly, and in the second work state, the motor 70 drives the cutting knife assembly to advance or retract without driving the end effector. Coupling includes a direct coupling and also includes an indirect coupling. Similarly, driving includes a direct driving and also includes an indirect driving.

Similar to the first embodiment, the surgical instrument in operation is operated in the following steps during a normal use process.

In S1, an output shaft of the motor 70 rotates in a first direction, and the motor 70 drives the first effective stroke structure and is coupled with the second idle stroke structure.

In S2, the output shaft of the motor 70 continues to rotate in the first direction, and the motor 70 drives the second effective stroke structure and is coupled with the first idle stroke structure.

In S3, the output shaft of the motor 70 rotates in a second direction, the second direction is opposite to the first direction, and the motor 70 drives the second effective stroke structure and is coupled with the first idle stroke structure.

In S4, the motor 70 continues to rotate in the second direction, and the motor 70 drives the first effective stroke structure and is coupled with the second idle stroke structure.

Therefore, during a normal use process of the surgical instrument in operation, the output shaft of the motor 70 is reversed (rotates in the first direction and the second direction respectively), and in each rotation direction of the motor 70, the first work state and the second work state are switched, so that the driving device is fully utilized, the structure of the driving device is simplified on the premise that the logic action relation between the end effector and the cutting knife assembly is satisfied, and the design is quite reasonable.

The surgical instrument performs step S1 such that the driving device drives the end effector to be closed, thereby clamping tissue.

The surgical instrument performs step S2 such that the driving device drives the cutting knife assembly to advance, thereby cutting the tissue.

The surgical instrument performs step S3 such that the driving device drives the cutting knife assembly to retract, thereby resetting the cutting knife assembly.

The surgical instrument performs step S4 such that the driving device drives the end effector to be opened, thereby releasing the tissue.

It can be seen that the driving device of the surgical instrument is quite reasonable in design, so that the driving device is fully utilized, and meanwhile, the functions required by the normal work of the surgical instrument are completely realized.

It is to be noted that the term "normal" work means that no other unexpected conditions, such as jamming of the cutting knife assembly, occur during the operation. The surgical instrument is deservedly designed with emergency devices to cope with unexpected conditions of the surgical instrument during the operation, but these emergency devices are not within the scope of the disclosure and not be described in detail.

Similar to the first embodiment, the driving device further includes a front driving gear, the front driving gear is always connected with the motor 70 and is driven by the motor 70, and the front driving gear drives the first driving device and the second driving device. The front driving gear of the driving device is the fifth gear 71. As long as the motor 70 is started such that its motor shaft rotates, the front driving gear (fifth gear 71) may drive one of the first effective stroke structure and the second effective stroke structure without driving both structures simultaneously. The motor 70 and the front driving gear are referred to as a power assembly. Therefore, the driving device of the disclosure realizes switching between the first effective stroke structure and the second effective stroke structure without disposing an additional clutch device, thereby not only simplifying the structure of the driving device, but also avoiding the instability caused by clutch operation and greatly improving the safety of the surgical instrument.

The second driving device in the embodiment has the same structure as the second driving device of the first embodiment.

In some embodiments, referring back to FIG. 9, the second driving device includes a second driving gear which is always meshed with the fifth gear 71 and is driven by the motor 70 through the fifth gear 71. Thus, the second driving gear is always connected with the motor 70 indirectly and driven by the motor 70. A sixth gear formed by a first tooth portion 959 of a first toothed portion 951 and a second toothed portion 954 forms a second driving gear, and the fifth gear 71 drives the second driving gear to rotate. The second driving device includes a second effective stoke structure and a second idle stoke structure, the second effective stoke structure is a second tooth portion 957 of the first toothed portion 951, and the second idle stoke structure is a non-toothed portion 953. The second driving device further includes a rack 91 driven by the second effective stoke structure. The details will not be elaborated herein.

It can be seen that the second driving device includes a second driving assembly, and a second motion conversion assembly engaged with the second driving assembly. In some embodiments, the second driving assembly includes a second driving member being a second driving gear, i.e., the sixth gear formed by the first tooth portion 959 of the first toothed portion 951 and the second toothed portion 954. The second motion conversion assembly includes a second transmission member and a second output member. In some embodiments, the second transmission member includes the second tooth portion 957 and the non-toothed portion 953, and the second output member includes the rack 91. The second driving member and the second transmission member are integrally disposed, so that the second driving member and the second transmission member synchronously move.

The second tooth portion 957 is the effective stroke structure, the non-toothed portion 953 is the idle stroke structure, so that, in the second driving device, the second effective stroke structure and the second idle stroke structure are disposed on the second motion conversion assembly, and particularly on the second transmission member of the second motion conversion assembly. The second effective stroke structure is engaged with the second output member, which moves, and the second output member is not driven when the second idle stroke structure is coupled with the second output member. In some embodiments, when the second tooth portion 957 is engaged with the rack 91, the second tooth portion 957 drives the rack 91 to move linearly; and when the non-toothed portion 953 is coupled with the rack 91, the rack 91 is not driven. It can be seen that the second transmission member formed by the second tooth portion 957 and the non-toothed portion 953 is always engaged with the fifth gear 71 through the second driving gear, regardless of whether the second tooth portion 957 is engaged with the rack 91 or the non-toothed portion 953 is coupled with the rack.

It is to be noted that in some embodiments of the disclosure, coupling means that no motion is transmitted between two components; whereas engaging means that two components are connected and motion may be transmitted. It is to be noted that, in some embodiments of the disclosure, coupling includes the direct coupling and the indirect coupling, when a component A and a component B in a same driving "chain" are adjacent to each other and do not contact each other, so that no motion is transmitted, the component A and the component B are the direct coupling, other components directly or indirectly driving the component A in the same driving "chain" are indirectly coupled with the component B, and the component A is indirectly coupled with other components directly or indirectly driven by the component B in the same driving "chain". Engaging includes a direct engaging and an indirect engaging, when a component C and a component D in the same driving "chain" are connected and motion may be transmitted, the component C and the component D are the direct engaging, other components directly or indirectly driving the component C in the same driving "chain" are indirectly engaged with the component D, and the component C is indirectly engaged with other components directly or indirectly driven by the component D in the same driving "chain". For example, the motor, the front driving gear, the first driving gear, the first driving assembly and the first motion conversion assembly form a driving "chain", and the motor, the front driving gear, the second driving gear, the second driving assembly and the second motion conversion assembly also form a driving "chain".

Although a speed reduction assembly including a third gear 97 and a fourth gear 98 is further disposed between the second tooth portion 957 and the rack 91, the speed reduction assembly only achieves speed reduction and does not affect the substantial operation principle of the second motion conversion assembly.

The first driving device in the embodiment is different in partial structure from the first embodiment.

As can be seen from the above description, in the first embodiment, the first driving device includes the first driving assembly and the first motion conversion assembly driven by the first driving assembly. The first motion conversion assembly includes a first transmission member and a first output member engaged with the first transmission member. In some embodiments, the first driving assembly includes the first gear 88. The first transmission member includes a straight groove 892 and an arc groove 891, and the first output member includes a protruding column 96. The first output member may be a direct output member of the first motion conversion assembly, such as the protruding column 96; and the first output member may also be an indirect output member of the first motion conversion assembly, such as a sleeve 22 or other subsequent output members.

In the first embodiment, the straight groove 892 is an effective stroke structure, the arc groove 891 is an idle stroke structure, that is, in the first embodiment, the effective stroke structure and the idle stroke structure are disposed on the motion conversion assembly. The motion conversion component realizes conversion of two different motion forms.

While in the embodiment, the first driving device is driven by the power assembly, and the first driving device includes the driving assembly and the motion conversion assembly driven by the first driving assembly. The motion conversion assembly includes a driving member and an output member. The driving assembly includes the first effective stroke structure and the first idle stroke structure. The first driving device has a first state and a second state. In the first state, when the power assembly is engaged with the first effective stroke structure, the driving assembly drives the motion conversion assembly, and the output member moves; and in the second state, the power assembly is coupled with the first idle stroke structure, the motion conversion assembly is disengaged from the driving of the power assembly, the driving assembly does not drive the motion conversion assembly, and the output member is not driven. That is, in the embodiment, the effective stroke structure and the idle stroke structure are disposed on the driving assembly. The driving assembly only transmits its previous form of motion without effecting the conversion of the form of motion.

For the first driving device of the embodiment, compared with the first embodiment, although in one embodiment, the effective stroke structure and the idle stroke structure are disposed on the driving assembly, in the other embodiment, the effective stroke structure and the idle stroke structure are disposed on the motion conversion assembly, there are some similarities between the disclosure conception of the embodiment and the first embodiment, i.e., the effective stroke structure and the idle stroke structure are disposed in a transmission chain of the driving device, so that the output member may also be driven or not driven as required even if the motor is driven.

In some embodiments, the driving assembly includes a first driving member and a rotating member 720, the effective stoke structure and the idle stoke structure are disposed on the rotating member 720, the first driving member and the rotating member 720 have two states, in a first state, the effective stoke structure of the rotating member 720 and the first driving member are synchronously driven by the motor 70, the rotating member 720 drives the motion conversion assembly, and the output member moves; and in a second state, the motor 70 is coupled with the idle stoke structure, the motor drives the first driving member and does not drive the rotating member 720, the rotating member 720 does not drive the motion conversion assembly, and the output member is not driven. When the motor 70 drives the first effective stroke structure, the motion conversion assembly converts rotation of the rotating member 720 into linear motion of the output member, and the linear motion of the output member further drives the end effector to be opened or closed. When the motor 70 is coupled with the first idle stoke structure, the motor 70 does not drive the sleeve to move.

In some embodiments, the first driving member is a first driving gear 732 which is always connected with the motor 70 and driven by the motor 70. More specifically, the first driving gear 732 is always meshed with the fifth gear 71, and the fifth gear 71 is always connected with the motor 70 and driven by the motor 70, so that the first driving gear 732 is indirectly connected with the motor 70 and driven by the motor 70.

The first effective stroke structure is a toothed portion 724, and the first idle stroke structure is a non-toothed portion 730. The toothed portion 724 and the non-toothed portion 730 are disposed on a circumferential face of the rotating member 720. The toothed portion 724 and the non-toothed portion 730 are disposed adjacently. The outer diameter of the non-toothed portion 730 is smaller than the outer diameter of the toothed portion 724, and the outer diameter of the toothed portion 724 includes the dimension, in a radial direction of the rotating member 720, of teeth.

The motion conversion assembly includes a transmission member and the output member, and the transmission member is disposed on the rotating member 720. The transmission member includes a first groove 722, and the output member includes a protruding column 86. A radial distance between the first groove 722 and a rotation center of the rotating member 720 increases or decreases along the first groove 722, and the protruding column 86 slides in the first groove 722 to convert rotation of the rotating member 720 into linear motion of the protruding column 86. The protruding column 86 is a direct output member. The protruding column 86 is connected with a connecting rod, a compression ring and the sleeve in sequence, which is the same as the first embodiment. The sequential connection means that: the connecting rod is connected with the protruding column 86, the compression ring is connected with the connecting rod, and the sleeve is connected with the compression ring. The sleeve may drive the end effector to be opened or closed. The sleeve may be considered an indirect output member.

In the first state, the toothed portion 724 of the rotating member 720 and the first driving gear 732 are simultaneously meshed with the fifth gear 71, the rotating member 720 and the first driving gear 732 are driven by the fifth gear 71 to synchronously rotate, the rotating member 720 is driven by the fifth gear 71 to rotate, i.e., the protruding column 86 may be driven to linearly move through the matching of the first groove 722 and the protruding column 86, and finally, the end effector is driven to be closed or opened; in the second state, only the first driving gear 732 is meshed with the fifth gear 71 and driven by the motor 70, while the non-toothed portion 730 of the rotating member 720 is coupled with the fifth gear 71 and indirectly coupled with the motor 70, the non-toothed portion 730 of the rotating member 720 may not be meshed with the fifth gear 71, and the rotating member 720 does not drive the end effector to be closed or opened. The meaning of coupling is consistent with the definition in the preceding text. It is also to be noted that, consistent with the foregoing description, coupling includes the direct coupling and the indirect coupling.

When the clinician uses the surgical instrument, the clinician typically operates a pressing holding mechanism to press the tissue after the end effector is closed and before the cutting knife assembly advances, during which the tissue is thinned and the end effector is further closed. To ensure that the driving gear always applies force to the end effector to keep the end effector in a closed state during a process of pressing tissue, referring to FIG. 24, in the embodiment, the first effective stroke structure includes a first portion and a second portion which are adjacently disposed, the first portion drives the end effector to execute a first stage of closing to clamp the tissue, and the second portion drives the end effector to execute a second stage of closing to press the tissue. In some embodiments, the toothed portion 724 includes a stroke driving tooth portion 726 and a pressing holding tooth portion 728 which are disposed adjacently. When the front driving gear drives the stroke driving tooth portion 726, the protruding column 86 slides in the first groove 722 to drive the end effector to be closed. The pressing holding tooth portion 728 is meshed with the front driving gear during pressing holding, so that the front driving gear always applies a certain action force on the end effector by the pressing holding tooth portion 728 during pressing holding, thereby avoiding an accidental release of the end effector. Since a closing stroke of the end effector is small during the process of pressing tissue, in the embodiment, the pressing holding tooth portion 728 includes one to two tooth portions.

The first groove 722 includes a first section and a second section communicated with the first section, corresponding to that "the first effective stroke structure includes the first portion and a second portion" disposed adjacently. The first portion is engaged with the power assembly, so that the first output member is engaged with the first section; and the second portion is engaged with the power assembly, so that the first output member is engaged with the second section. In some embodiments, the stroke driving tooth portion 726 is engaged with the fifth gear 71 and the motor 70 such that the protruding column 86 moves in in the first section, thereby driving the end effector to execute the first stage of closing; and the pressing holding tooth portion 728 is engaged with the fifth gear 71 and the motor 70 such that the protruding column 86 moves in the second section, thereby driving the end effector to execute the first stage of closing.

The end effector is driven to be closed for clamping tissue when the protruding column 86 moves in the first section, and is driven to be further closed to press the tissue when the protruding column 86 moves in the second section.

In some embodiments, the first groove 722 also includes a third section communicating with the second section, and the second section is located between the first section and the third section. The third section disposed may provide a certain margin for the sliding of the protruding column 86 in the first groove 722, so as to avoid jamming.

The first driving gear 732 and the rotating member 720 are overlapped, In some embodiments, the first driving gear 732 and the rotating member 720 are overlapped in the axial direction. It is convenient to mesh the first driving gear 732 and the toothed portion 724 of the rotating member 720 with the fifth gear 71 at the same time.

A first end face of the first driving gear 732 is adjacent to a second end face of the rotating member 720, one of the two end faces is provided with a second arc groove 734, the other is provided with a protrusion 736 extending into the second arc groove 734, and a circle center of the second arc groove 734 is located on the rotation axis of the first driving gear 732. The protrusion 736 may slide in the second arc groove 734. On one hand, the matching of the protrusion 736 with the second arc groove 734 may guarantee that the first driving gear 732 and the rotating member 720 are overlapped; on the other hand, the protrusion 736 may slide in the arc groove, so that in the second state, the rotating member 720 does not rotate with the first driving gear 732, the operation of the first idle stroke is guaranteed, and therefore, the rotating member 720 does not drive the end effector to be closed or opened when the driving device drives the cutting knife assembly to move.

Returning to FIGS. 7 and 8, in the first embodiment, the first gear 88 drives the sleeve to move linearly to drive the end effector to be opened or closed through sliding of the protruding column 86 in the straight groove 892, so that the first gear 88 applies an action force to the sleeve and thus the end effector. As can be known from the principle of action force and reverse force, the end effector, in turn, indirectly applies a certain reverse force to the first gear 88. When the cutting knife assembly cuts the tissue, the end effector clamps the tissue, and the clamping of the tissue is realized by the cooperation of the cutting knife assembly and the end effector in the cutting process. In some embodiments, the cutting knife assembly is provided with an upper lug portion, a lower lug portion and a connecting portion connected to the upper lug portion and the lower lug portion, and the upper lug portion, the lower lug portion and the connecting portion are fixedly connected or integrally formed. During cutting, the upper lug portion of the cutting knife assembly moves in the groove of a staple abutting seat of the end effector, and the lower lug portion moves in the groove of a staple cartridge seat. The upper lug portion has a traction effect on the staple abutting seat through the groove of the staple abutting seat, and the lower lug portion has a traction effect on the staple cartridge seat through the groove of the staple cartridge seat, so that mutual clamping of the staple abutting seat and the staple cartridge seat in the cutting process is realized. The reverse force of the tissue to the end effector is transmitted inversely through the first gear 88 to the fifth gear 71 and the motor 70, which reduces the power transmitted by the fifth gear 71 through the second driving device to the cutting knife assembly, thereby affecting the cutting efficiency of the cutting knife assembly.

Referring to FIGS. 21 to 23, in the embodiment, the protrusion 736 may freely slide in the second arc groove 734. Thus, there is a loose fit between the first driving gear 732 and the rotating member 720. Thus, even if the end effector clamps the tissue when the cutting knife assembly cuts the tissue, the reverse force applied by the end effector to the rotating member 720 is not transmitted to the fifth gear 71 or only a small portion of the reverse force is transmitted to the fifth gear 71 due to the loose fit between the rotating member 720 and the first driving gear 732, thereby avoiding or reducing the influences on the cutting efficiency of the cutting knife assembly and improving the cutting efficiency of the cutting knife assembly.

The width of the protrusion 736 is smaller than a width of the second arc groove 734. Thus, the protrusion 736 may slide in the second arc groove 734, and the function of the second state is realized. Those skilled in the art may appreciate that the width of the protrusion 736 is equal to the width of the second arc groove 734, and all the solutions similar to or the same as the present embodiments are covered within the protection scope of the disclosure.

When the driving device drives the second effective stroke structure, the protrusion 736 slides in the second arc groove 734. In the embodiment, a circumferential extension length of the second arc groove 734 is greater than a circumferential extension length required by the second effective stroke. Margin is provided for movement of the projection 736 in the second arc groove 734. Those skilled in the art may appreciate that the circumferential extension length of the second arc groove 734 is equal to the circumferential extension length of the second effective stroke, and all the solutions similar to or the same as the present embodiments are covered in the protection scope of the disclosure.

The protrusion 736 abuts against an end portion of the second arc groove 734 so that the rotating member 720 and the first driving gear 732 are switched from the second state to a ready position of the first state. In some embodiments, after retracting is completed, the protrusion 736 abuts against a head end 742 of the second arc groove 734, so that the toothed portion 724 of the rotating member 720 and the teeth of the first driving gear 732 are aligned up and down, and at the moment, if the motor 70 rotates, the rotating member 720 and the first driving gear 732 are synchronously meshed with the front driving gear 71, so as to ensure the subsequent smooth opening of the end effector to release the tissue.

Therefore, in the embodiment, the toothed portion 724 of the rotating member 720 is the first effective stroke structure, and the non-toothed portion 730 of the rotating member 720 is the first idle stroke structure. The first driving gear 732 is always meshed with the fifth gear 71 and is driven by the motor 70, so that the effective stroke and the idle stroke are conveniently switched, and the structural design is reasonable.

The associated work process of the surgical instrument of the embodiment will now be described with reference to FIGS. 24-27.

Figure 24:
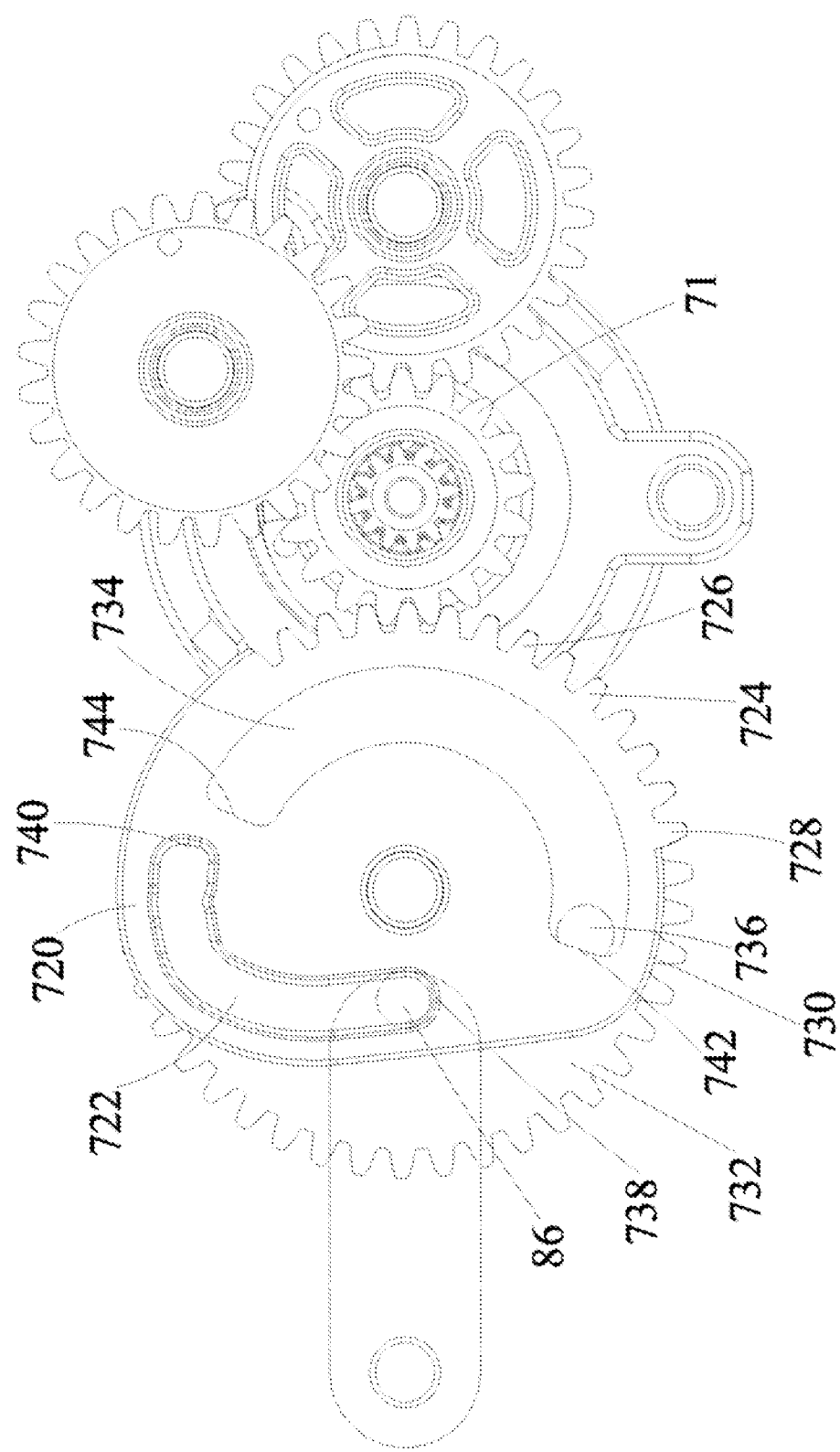
FIGS. 24-28 illustrate schematic diagrams of state changes of a first driving device of the stapler as shown in FIG. 21.

As shown in FIG. 24, at the moment, the end effector is in an open state and the cutting knife assembly is in an initial position. In the first driving device, the protruding column 86 is located at a first end 738 of the first groove 722, the protrusion 736 is located at a head end 742 of the second arc groove 734, and the toothed portion 724 of the rotating member 720 and the first driving gear 732 are simultaneously meshed with the driving gear (the fifth gear 71).

At the moment, if the clinician determines that the end effector has been aligned with the tissue to be cut, the clinician starts the motor 70, the motor 70 rotates in the first direction to drive the driving gear (the fifth gear 71) to rotate, the rotating member 720 and the first driving gear 732 are in a first state, and the driving gear (the fifth gear 71) rotates to simultaneously drive the rotating member 720 and the first driving gear 732 to rotate. In the process, there is no relative rotation of the rotating member 720 and the first driving gear 732, and thus, the protrusion 736 remains at the head end 742 of the second arc groove 734; while rotation of the rotating member 720 drives the protruding column 86 to move in the first groove 722 from a first end 738 toward a second end 740, the end effector is gradually closed, and the first driving device reaches the position shown in FIG. 25.

Figure 25:
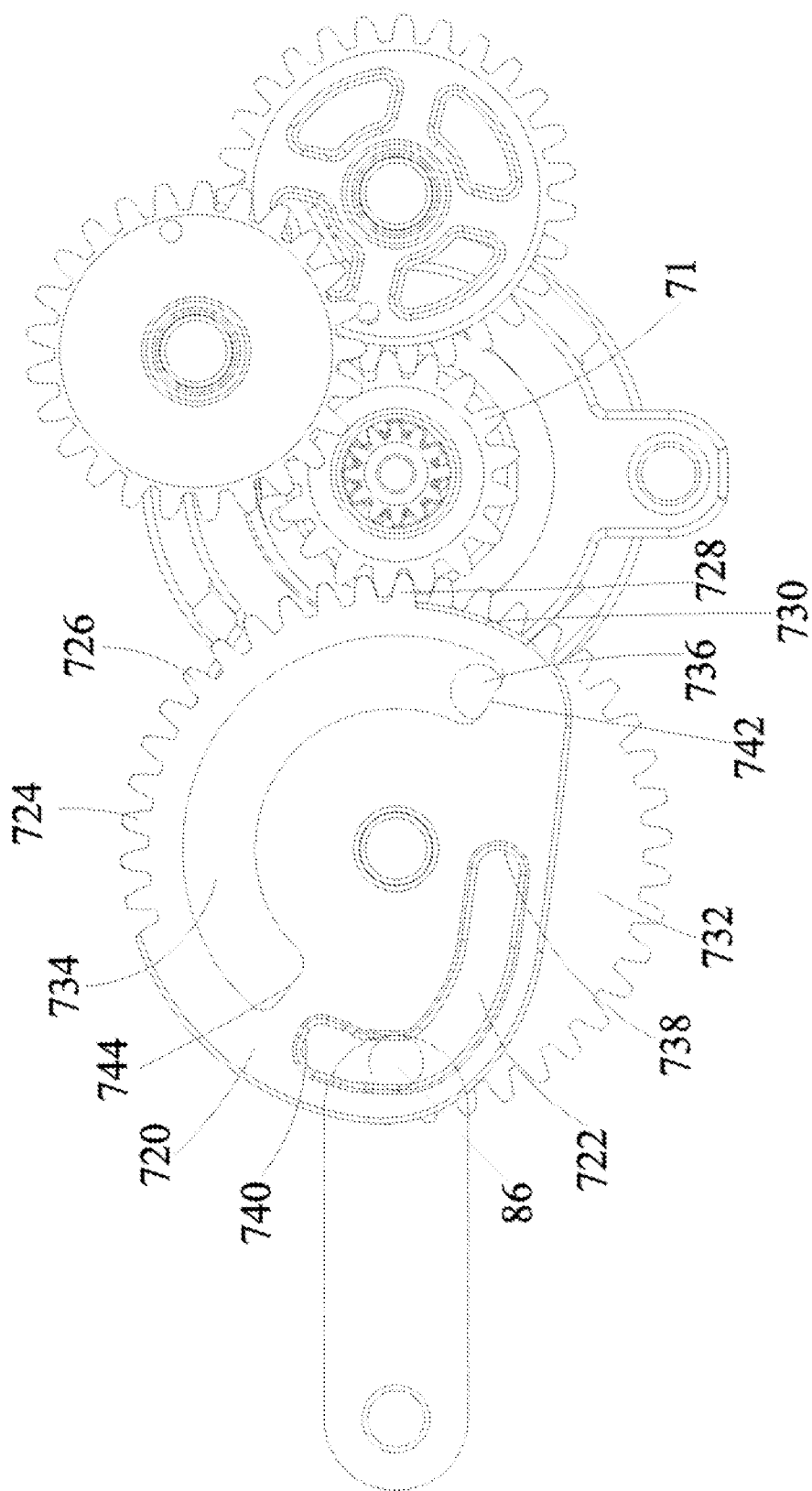

At the position shown in FIG. 25, the driving gear (the fifth gear 71) is still meshed with the toothed portion 724, in some embodiments, the driving gear (the fifth gear 71) is still meshed with the pressing holding tooth portion 728 of the toothed portion 724. At the moment, the clinician may operate the pressing holding mechanism, during which the driving gear (the fifth gear 71) simultaneously drives the pressing holding tooth portion 728 and the first driving gear 732, the protruding column 86 moves a short distance further toward the second end 740, and the end effector is further closed to reach the position shown in FIG. 26.

Figure 26:
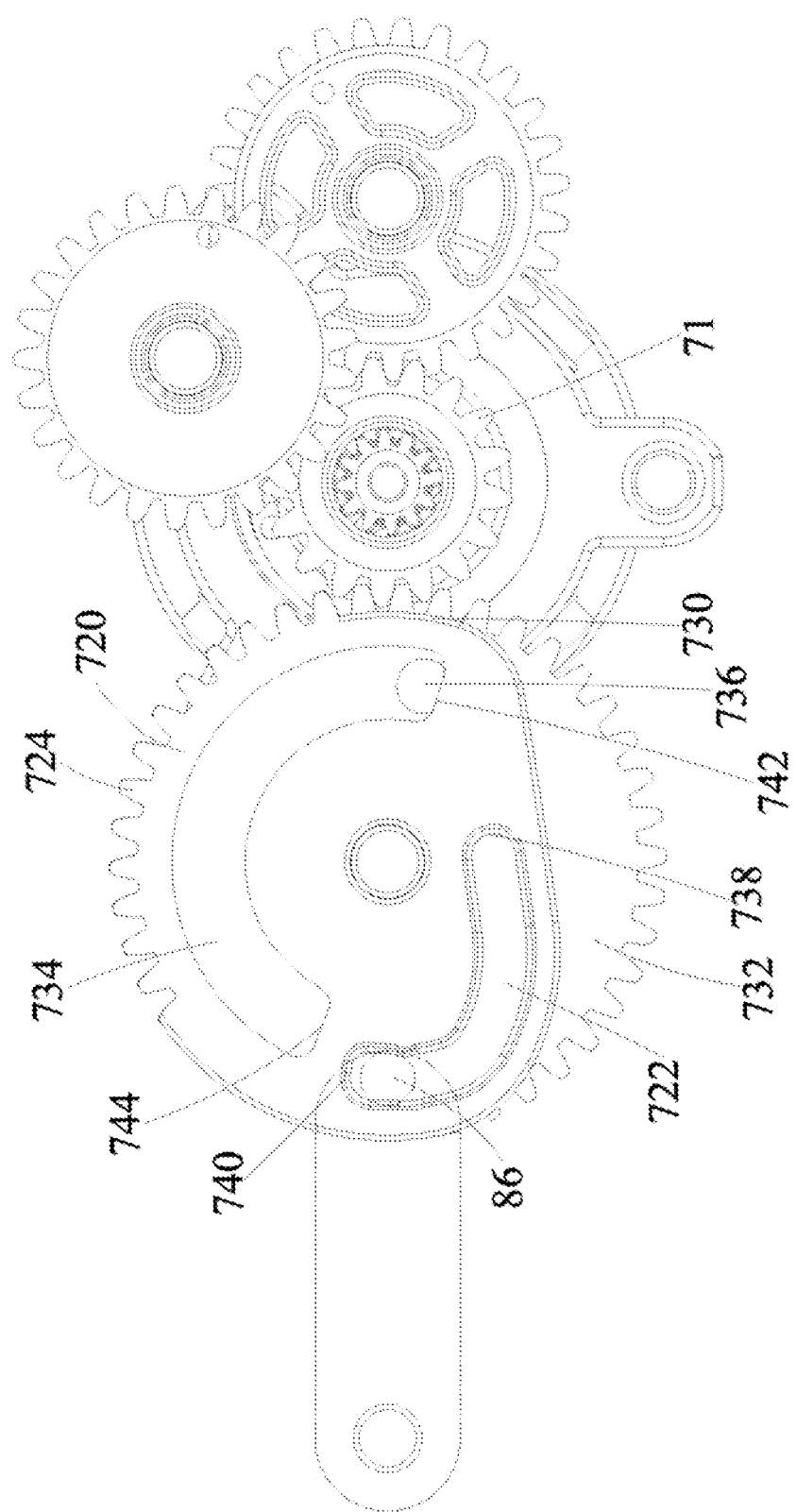

In the position shown in FIG. 26, the end effector has pressed the tissue, the rotating member 720 and the first driving gear 732 are switched from the first state to the second state, the driving gear (the fifth gear 71) is disengaged from the toothed portion 724 of the rotating member 720, and the driving gear (the fifth gear 71) is only meshed with the first driving gear 732. At the moment, the clinician may operate the cutting knife assembly, the motor 70 continues to rotate in the first direction, the motor 70 drives the cutting knife assembly to advance through the same second driving device (only part of which is shown in FIG. 26) as in the first embodiment, so that the cutting knife assembly moves from an initial position to a final position, during the process, the non-toothed portion 730 is coupled with the driving gear (the fifth gear 71), the driving gear (the fifth gear 71) does not drive the end effector to move through the non-toothed portion 730, but the driving gear (the fifth gear 71) drives the first driving gear 732 of the first driving device to rotate, and the protrusion 736 is driven to slide in the second arc groove 734 from a head end 742 toward a tail end 744 to reach the position shown in FIG. 27.

Figure 27:
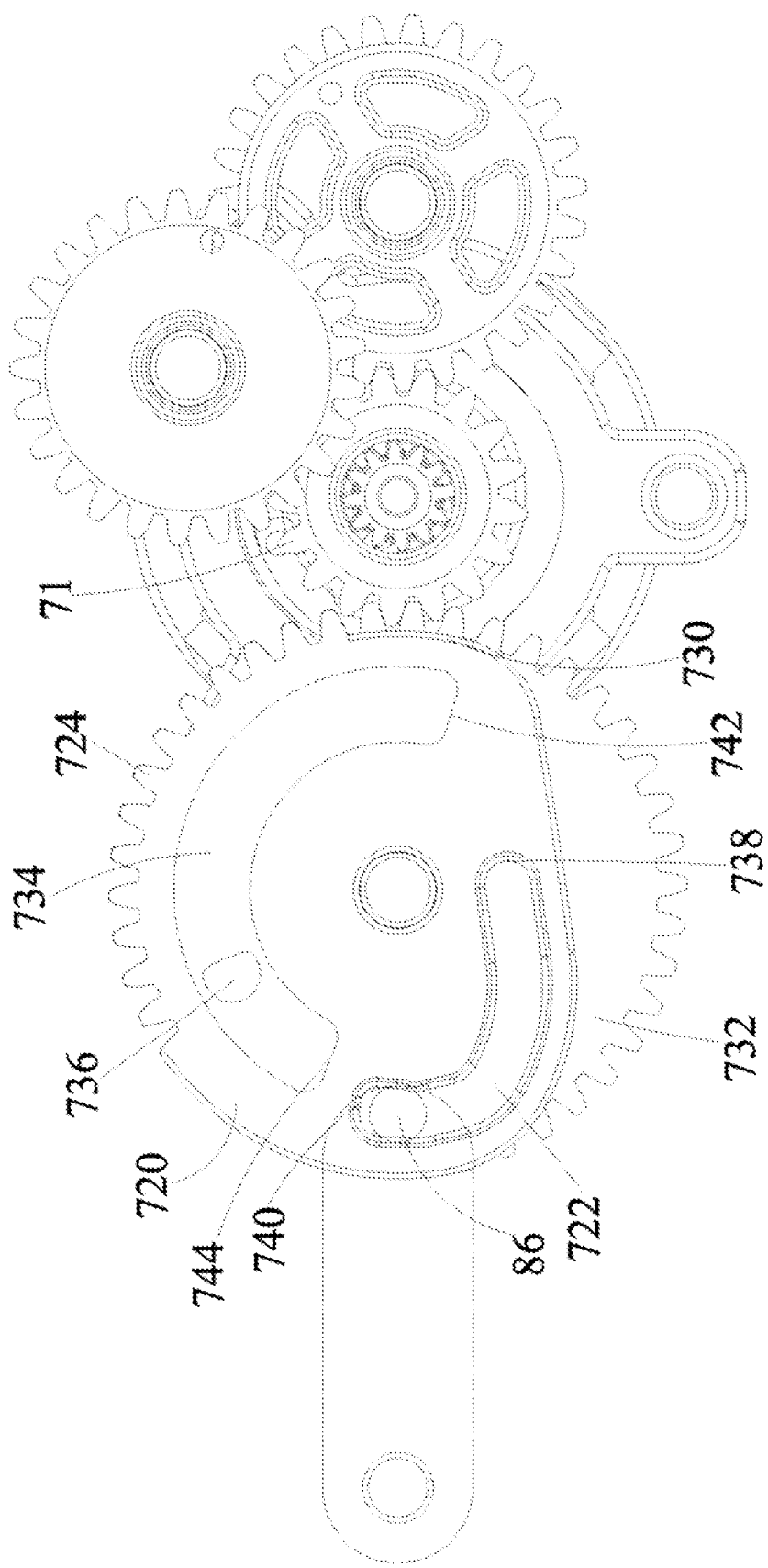

At the position shown in FIG. 27, the cutting assembly is at the final position and the tissue is cut. At the moment, the clinician may operate the motor 70 to rotate reversely, i.e., in the second direction opposite to the first direction, the motor 70 drives the cutting knife assembly to retract through the same second driving device (only part of which is shown in FIG. 27) as in the first embodiment, so that the cutting knife assembly retracts to the initial position from the final position, during which the non-toothed portion 730 is coupled with the driving gear (the fifth gear 71), the driving gear (the fifth gear 71) does not drive the end effector to move through the non-toothed portion 730, but the driving gear (the fifth gear 71) drives the first driving gear 732 of the first driving device to rotate reversely, and the protrusion 736 is driven to slide in the second arc groove 734 towards the head end 742, and when the protrusion 736 abuts against the head end 742 of the second arc groove 734, the toothed portion 724 of the rotating member 720 and the tooth portion of the first driving gear 732 are aligned up and down, and the protrusion 736 reaches the position shown in FIG. 28.

Figure 28:
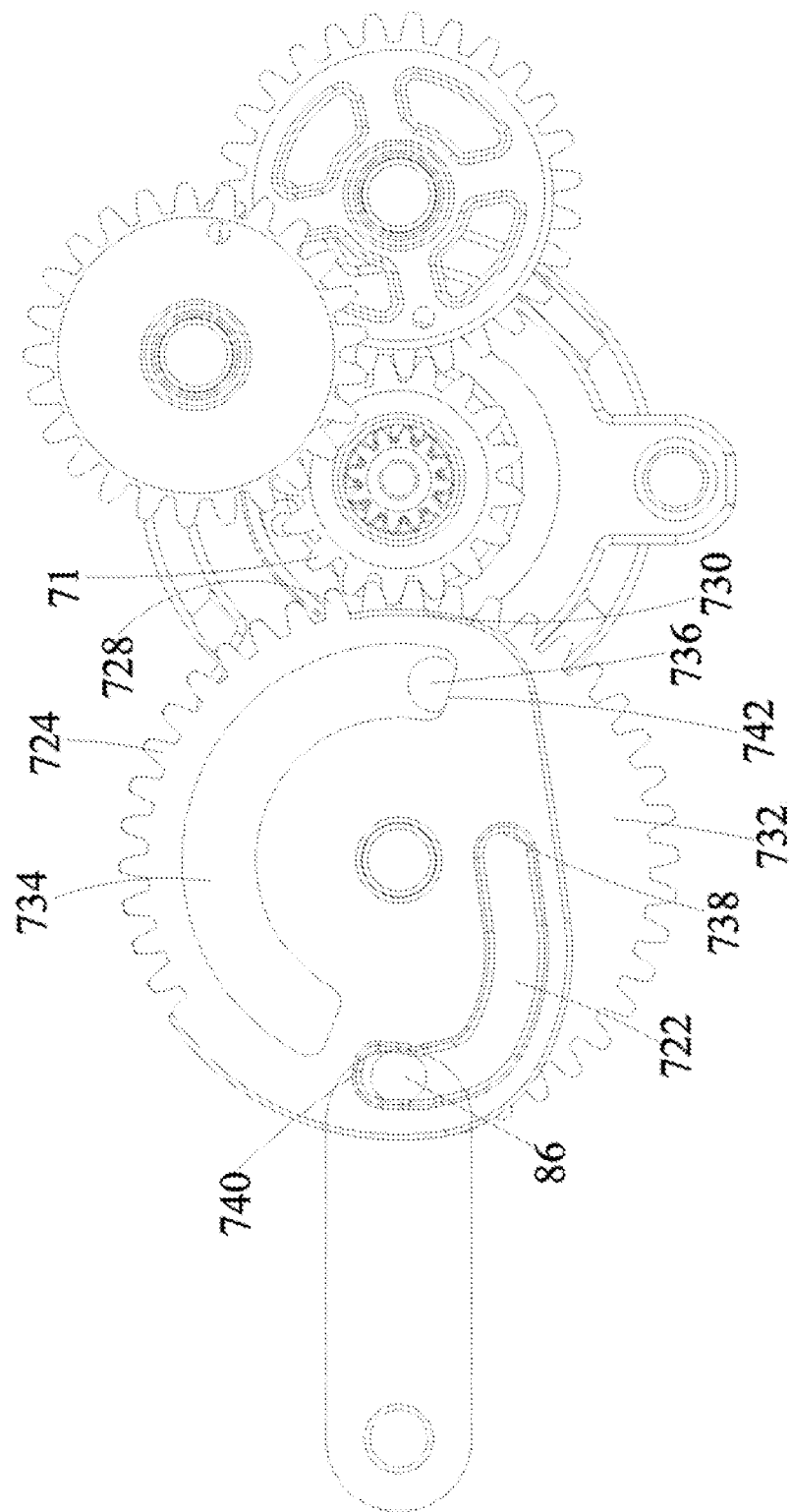

At the position shown in FIG. 28, the clinician may operate the motor 70 such that the motor 70 continues to rotate reversely, the driving gear (the fifth gear 71) begins to drive the rotating member 720 and the first driving gear 732 to simultaneously rotate reversely, the protrusion 736 remains at the head end 742 of the second arc groove 734, and the protruding column 86 moves in the first groove 722 in a direction towards the first end 738, thereby driving the end effector to be opened, returning to the state shown in FIG. 24. Thus, a complete operation of the surgical instrument is realized, during which the surgical instrument sequentially realizes closing of the end effector for clamping the tissue, advancing of the cutting knife assembly for cutting the tissue, retracting of the cutting knife assembly, and opening of the end effector for loosening the tissue.

In the second to third embodiments, except for the technical features already described in the embodiments and the technical features that may be substituted with the above-described technical features, other technical features in the above-described embodiments are in the same part as in the first embodiment and are not repeated.

In summary, the stapler 100 of the disclosure is provided with one motor 70 that driving the first driving work 80 to work, thereby driving the end effector 30 to be opened and closed, and can also drive the second driving device 90 to work, thereby driving the cutting knife assembly 40 to move forwards and backwards. The stapler 100 of the disclosure is small in size and low in cost, and in addition, one motor 70 enables the stapler 100 to be small in overall weight and flexible to operate by the clinician. Single-motor driving is achieved by disposing the gear structure in the driving device, and the first driving device and the second driving device are simple in structure.

The embodiments of the disclosure have been shown or described above. However, it can be understood that the abovementioned embodiments are exemplary and should not be understood as limits to the disclosure, and those of ordinary skill in the art may make variations, modifications, replacements, transformations to the abovementioned embodiments within the scope of the disclosure, and the technical solutions after the variations, modifications, replacements, transformations are all within the protection scope of the disclosure.

What is claimed is:

1. A driving device, driven by a power assembly, the driving device comprising a first driving assembly and a first motion conversion assembly, wherein the first driving assembly comprises a first effective stroke structure and a first idle stroke structure, the driving device has a first state and a second state, in the first state, the power assembly is engaged with the first effective stroke structure, and the first effective stroke structure drives the first motion conversion assembly; and in the second state, the power assembly is coupled with the first idle stroke structure, and the first motion conversion assembly is disengaged from a driving of the power assembly; wherein the first driving assembly comprises a first driving member and a rotating member, and in the first state, the first driving member and the rotating member are both engaged with the power assembly; and in the second state, only the first driving member of the first driving member and the rotating member is engaged with the power assembly.

2. The driving device as claimed in claim 1, wherein the first motion conversion assembly comprises a first transmission member and a first output member, and in the first state, the first transmission member drives the first output member to move; and in the second state, the first output member is not driven.

3. The driving device as claimed in claim 1, wherein the first effective stroke structure and the first idle stroke structure are both disposed on the rotating member, and in the first state, the first effective stroke structure and the first driving member are both engaged with the power assembly; and in the second state, the first idle stroke structure is coupled with the power assembly, and the first driving member is engaged with the power assembly.

4. The driving device as claimed in claim 3, wherein the first effective stroke structure is a toothed portion, the first idle stroke structure is a non-toothed portion, and the toothed portion and the non-toothed portion are disposed adjacently; and the first driving member is a first driving gear.

5. The driving device as claimed in claim 4, wherein the power assembly comprises a motor and a front driving gear driven by the motor, and in the first state, the front driving gear is meshed with the toothed portion and the first driving gear simultaneously; and in the second state, the front driving gear is coupled with the non-toothed portion, and is meshed with the first driving gear.

6. The driving device as claimed in claim 3, wherein the first motion conversion assembly comprises a first groove and a protruding column, a radial distance between the first groove and a rotation center of the rotating member increases or decreases along the first groove, and the protruding column slides in the first groove to convert rotation of the rotating member into linear movement of the protruding column.

7. The driving device as claimed in claim 6, wherein the first groove is disposed on the rotating member.

8. The driving device as claimed in claim 1, wherein the first driving member and the rotating member are overlapped, one of the first driving member and the rotating member is provided with an arc groove, the other is provided with a protrusion extending into the arc groove, and a circle center of the arc groove is located on a rotation axis of the first driving member.

9. The driving device as claimed in claim 8, wherein a width of the protrusion is smaller than a width of the arc groove; or the protrusion abuts against an end portion of the arc groove, so that the rotating member and the first driving member are switched from the second state to a ready position of the first state.

10. An end actuator driving device, comprising the driving device as claimed in claim 1, wherein the driving device is configured to drive an end actuator to be opened or closed.

11. The end actuator driving device as claimed in claim 10, wherein the first effective stroke structure comprises a first portion and a second portion which are disposed adjacently, the first portion drives the end actuator to execute a first stage of closing to clamp tissue, and the second portion drives the end actuator to execute a second stage of closing to press the tissue.

12. The end actuator driving device as claimed in claim 11, wherein the first motion conversion assembly comprises a first transmission member and a first output member engaged with the first transmission member, and the first transmission member comprises a first section and a second section which are disposed adjacently; the first portion is engaged with the power assembly, so that the first output member is engaged with the first section; and the second portion is engaged with the power assembly, so that the first output member is engaged with the second section.

13. The end actuator driving device as claimed in claim 12, wherein the first transmission member also comprises a third section adjacent to the second section, and the second section is located between the first section and the third section.

14. A surgical instrument driving device, comprising the end actuator driving device as claimed in claim 10; wherein the surgical instrument driving device comprises a cutting knife assembly driving device, which drives a cutting knife assembly to move forwards or backwards.

15. The surgical instrument driving device as claimed in claim 14, wherein the cutting knife assembly driving device is driven by a power assembly; wherein the cutting knife assembly driving device comprises a second effective stroke structure and a second idle stroke structure, and the power assembly drives one of the first effective stroke structure and the second effective stroke structure.

16. The surgical instrument driving device as claimed in claim 14, wherein the cutting knife assembly driving device comprises a second driving assembly and a second motion conversion assembly engaged with the second driving assembly, the second motion conversion assembly comprises a second transmission member and a second output member, the second transmission member comprises a second effective stroke structure and a second idle stroke structure, the cutting knife assembly driving device has a third state and a fourth state, and in the third state, the second effective stroke structure is engaged with the second output member; and in the fourth state, the second idle stroke structure is coupled with the second output member.

17. The surgical instrument driving device as claimed in claim 16, wherein the second driving assembly comprises a second driving member, the second driving member and the second transmission member move synchronously, and in the third state and the fourth state, the second transmission member is always engaged with the power assembly through the second driving member.

18. The surgical instrument driving device as claimed in claim 16, wherein the second effective stroke structure is a toothed portion disposed on the second transmission member, the second idle stroke structure is a non-toothed portion disposed on the second transmission member, and the second output member is a rack.

19. A surgical instrument, comprising a transmission mechanism, an end actuator driven by the transmission mechanism, and a cutting knife assembly, wherein the transmission mechanism comprises the surgical instrument driving device as claimed in claim 14.

\* \* \* \* \*